(12) United States Patent
Lin et al.

(10) Patent No.: US 10,376,577 B2
(45) Date of Patent: Aug. 13, 2019

(54) REFINED PRODUCT OBTAINED FROM RICE HULL AND PREPARATION PROCESS AND USE THEREOF

(71) Applicant: China Medical University, Taichung (TW)

(72) Inventors: Wen-Chuan Lin, Taichung (TW); Li-Chan Yang, Taichung (TW); Chang-Chi Hsieh, Taichung (TW)

(73) Assignee: China Medical University, Taichung (TW)

( * ) Notice: Subject to any disclaimer, the term of this patent is extended or adjusted under 35 U.S.C. 154(b) by 734 days.

(21) Appl. No.: 14/831,275

(22) Filed: Aug. 20, 2015

(65) Prior Publication Data

US 2016/0060367 A1 Mar. 3, 2016

(30) Foreign Application Priority Data

Aug. 26, 2014 (TW) .............................. 103129334 A

(51) Int. Cl.
*A61K 36/899* (2006.01)
*A61K 39/39* (2006.01)
*A61K 31/715* (2006.01)
*C12P 19/14* (2006.01)
*C12P 19/04* (2006.01)
*C08B 37/00* (2006.01)
*A61K 39/00* (2006.01)

(52) U.S. Cl.
CPC ............ *A61K 39/39* (2013.01); *A61K 31/715* (2013.01); *A61K 36/899* (2013.01); *C08B 37/0003* (2013.01); *C08B 37/006* (2013.01); *C12P 19/04* (2013.01); *C12P 19/14* (2013.01); *A61K 2039/55583* (2013.01)

(58) Field of Classification Search
CPC .................................................... A61K 36/899
USPC ........................................................ 424/750
See application file for complete search history.

(56) References Cited

U.S. PATENT DOCUMENTS

2011/0082103 A1* 4/2011 Lin ...................... A61K 31/715
514/54
2011/0171709 A1* 7/2011 Bardsley ................... C12P 7/10
435/165

OTHER PUBLICATIONS

Grieshop et al. (Oral Administration of Arabinogalactan Affects Immune Status and Fecal Microbial Populations in Dogs, The Journal of Nutrition, vol. 132, Issue 3, Mar. 1, 2002, pp. 478-482) (Year: 2002).*

* cited by examiner

*Primary Examiner* — Michael Barker
*Assistant Examiner* — Deborah A Davis
(74) *Attorney, Agent, or Firm* — Cesari and McKenna, LLP

(57) ABSTRACT

Disclosed herein is a refined product obtained from a rice hull, which consists essentially of a type II arabinogalactan having a number average molecular weight in the range of 56 to 103 kDa. Also disclosed are a process for producing the refined product and use of the refined product for enhancing the biological activity of innate immune cells, as well as for treating allergy and cancer.

4 Claims, 12 Drawing Sheets ued States Patent US 10,376,577 B2

REFINED PRODUCT OBTAINED FROM RICE HULL AND PREPARATION PROCESS AND USE THEREOF

CROSS-REFERENCE TO RELATED APPLICATION

This application claims priority of Taiwanese Application No. 103129334, filed on Aug. 26, 2014.

FIELD

The present disclosure relates to a refined product obtained from a rice hull and a preparation process thereof. The present disclosure also relates to use of the refined product for enhancing the biological activity of innate immune cells, as well as for treating allergy and cancer.

BACKGROUND

Arabinogalactans are polysaccharides composed of arabinose and galactose, and exist in a variety of plants (such as *Larix occidentalis, Baptisia tinctoria, Echinacea purpurea*, and *Curcuma longa*). It has been reported that arabinogalactans are effective in treating intestinal disorders (such as diverticulosis and irritable bowel syndrome), enhancing the activity of the human immune system, and inhibiting metastasis of liver tumor cells, thereby being able to serve as dietary fiber, an immunomodulator, and a therapeutic agent for cancer (Pal, A. (2008). Chapter 13. Arabinogalactan Protein and Arabinogalactan: Biomolecules with Biotechnological and Therapeutic Potential. In K. G. Ramawat and J. M. Merillon (Eds.) *Bioactive molecules and medicinal plants* (pp 255-270) Springer).

Arabinogalactans are classified into the following two categories according to structure:
(1) type I arabinogalactans (also referred to as arabino-4-galactan), which contain 1,4-linked galactose residues serving as a backbone and forming a straight chain; and
(2) type II arabinogalactans (also referred to as arabino-3,6-galactan), which contain 1,3-linked or 1,6-linked galactose residues serving as a backbone, and which are normally attached to a protein to form an arabinogalactan protein.

Arabinogalactan proteins have been successfully isolated from organisms by the researchers in this field. For instance, as reported in Birgit Classen et al. (2000), *Carbohydrate Research*, 327:497-504, the pressed juice of *Echinacea purpurea* was subjected to tangential cross flow filtration to obtain a high molecular weight fraction, and the β-glucosyl Yariv reagent was subsequently used to perform precipitation on the high molecular weight fraction, such that an arabinogalactan protein was isolated. The arabinogalactan protein was subjected to molecular weight determination, chemical composition analysis, and linkage analysis. It was found from the results of molecular weight determination that the arabinogalactan protein has a molecular weight of $1.2 \times 10^3$ kDa. Furthermore, it was found from the results of chemical composition analysis that the arabinogalactan protein contains 83% (w/w) of a type II arabinogalactan, which has a molar ratio of galactose to arabinose being 1.8:1. In addition, it was found from the results of linkage analysis that most of the galactose residues of the arabinogalactan protein are 3,6-linked galactose residues.

As described in Kiyoshi Mashiguchi et al. (2004), *Plant Cell Physiol.*, 45:1817-1829, rice bran of japonica rice was homogenized, and the resultant homogenate was subsequently centrifuged, followed by collecting the supernatant thus formed. Precipitation was conducted using ethanol, and 20 mM Tris-HCl (containing 1% (v/v) Triton X-100; pH 8) was added to the resultant precipitate, followed by centrifugation. The resultant supernatant was collected, and $CaCl_2$ was added to the collected supernatant, followed by centrifugation. The supernatant thus formed was collected and was subjected to dialysis against deionized water. Afterward, a concentration process was conducted under vacuum. A 1 mM β-glucosyl Yariv reagent (β-GlcY) and 1% (w/v) NaCl were added to the resultant concentrate, followed by centrifugation. The pellet thus formed was collected, and dimethyl sulfoxide, sodium dithionate, and water were added thereto, such that a pale yellow solution was obtained. Subsequently, dialysis was conducted against deionized water. A solution containing β-glucosyl Yariv-reactive proteins was obtained and was subjected to reverse phase high performance liquid chromatography (RP HPLC). Consequently, three fractions, i.e. Fr. A to Fr. C, were obtained. Fr. A was subjected to deglycosylation, and the resultant deglycosylated Fr. A was subjected to N-terminal sequencing. The sequencing data thus obtained were compared with the known sequences in the rice cDNA database of KOME (knowledge-based *Oryza* molecular biological encyclopedia), thereby verifying that the β-glucosyl Yariv-reactive proteins in Fr. A are classical arabinogalactan proteins.

As disclosed in WO 2011/139168 A1, each of five honey samples (i.e. 0.5 year-old manuka honey, 2.5 year-old manuka honey, 5 year-old manuka honey, 1.5 year-old kanuka honey, and 1 year-old clover honey) was subjected to centrifugal ultrafiltration, followed by collecting fractions having a molecular weight greater than 10 kDa. Therefore, high molecular weight fractions were obtained. Subsequently, the high molecular weight fractions were subjected to salt precipitation, and the resultant precipitates were removed. A further precipitation process was conducted using the Yariv reagent, such that arabinogalactan proteins were obtained. It was proved by in vitro cell study that the arabinogalactan proteins stimulate the release of TNF-α from cells and hence have a pro-inflammatory effect. Furthermore, via gas chromatography-mass spectrometry analysis (GC-MS analysis) and glycosyl linkage analysis, it was proved that the high molecular weight fractions contain a type II arabinogalactan.

In addition, the researchers in this field have found that type II arabinogalactans exist in organisms. For instance, as reported in Esther Marie Goellner et al. (2011), *Carbohydrate Polymers*, 86:1739-1744, wood chips of *Larix laricina* were subjected to aqueous extraction, and an aqueous extract was hence obtained. Afterward, ethanol was added to the aqueous extract so as to form a precipitate having a high molecular weight, and the precipitate was subjected to molecular mass determination, monosaccharide composition analysis, and linkage analysis. It was verified by the results thus obtained that the precipitate contains a type II arabinogalactan. Particularly, it was found from the results of monosaccharide composition analysis that the type II arabinogalactan in the precipitate is composed of galactose, arabinose, and a small amount of glucuronic acid, and has a molar ratio of galactose to arabinose being 6:1. Moreover, it was found from the results of linkage analysis that the type II arabinogalactan in the precipitate contains 3,6-linked galactose residues, 1,6-linked galactose residues, terminally linked galactose residues, and a small amount of 1,3-linked galactose residues.

TW I379688 B1 discloses a polysaccharide extract of *Anoectochilus formosanus* for stimulating the release of granulocyte colony-stimulating factor (G-CSF). The polysaccharide extract of *Anoectochilus formosanus* is prepared using the following method. A sample of *Anoectochilus formosanus* is subjected to extraction with water so as to obtain a water-soluble extract. Subsequently, ethyl acetate is added to the water-soluble extract so as to conduct a partitioning process. The resultant aqueous phase is collected, and ethanol is added thereto. Afterward, the resultant precipitate is acquired and is dissolved in water. Furthermore, as shown in the examples of TW I379688 B1, the polysaccharide extract of *Anoectochilus formosanus* thus obtained was subjected to enzymatic hydrolysis using amylase, amyloglucosidase, and protease, followed by adding ethanol to the resultant hydrolysate. After the thus obtained precipitate was dissolved in water, a polysaccharide yet to be purified and having an average molecular weight of 29 kDa (hereinafter referred to as *Anoectochilus formosanus* polysaccharide) was acquired. It has been verified via experiments that *Anoectochilus formosanus* polysaccharide contains a type II arabinogalactan, and is capable of stimulating macrophages to release nitrogen monoxide and G-CSF, as well as reducing the concentration of tumor necrosis factor-α (TNF-α) in the blood of mice. Therefore, *Anoectochilus formosanus* polysaccharide is effective in activating innate immune cells and has anti-inflammatory activity.

Yang L. C. et al. (2013), *Evid. Based Complement Alternat. Med.*, 2013:458075 and Yang L. C. et al. (2014), *Phytomedicine*, 21:647-655 are two relevant journal articles which describe the follow-up study conducted by the research team for the invention of TW I379688 B1. As reported in Yang L. C. et al. (2013), supra, cells of mouse colon carcinoma cell line CT26 were inoculated into mice to induce colon cancer, followed by intraperitoneally injecting 5-fluorouracil (5-FU) into the mice and orally administering *Anoectochilus formosanus* polysaccharide so as to investigate the synergistic anticancer effect of *Anoectochilus formosanus* polysaccharide and 5-FU on colon cancer cells. The experimental results indicate that *Anoectochilus formosanus* polysaccharide is able to effectively reduce the leukopenia caused by 5-FU. As set forth in Yang L. C. et al. (2014), supra, *Anoectochilus formosanus* polysaccharide was further purified by virtue of anion exchange chromatography, such that a type II arabinogalactan was obtained. It was proved by experiments that the type II arabinogalactan has innate immuno-modulatory activity and anti-colon cancer activity.

Rice hulls are the protecting covering of grains of rice, and are normally used as building material, insulation material, fertilizer, and fuel. Through research, the inventor has obtained a refined product from a rice hull. The refined product consists essentially of a type II arabinogalactan having a number average molecular weight ranging from 56 to 103 kDa. Particularly, the type II arabinogalactan in the refined product has a physical/chemical property (e.g. the ratio of galactose to arabinose and the backbone) different from that of the conventional type II arabinogalactans in other organisms, and is effective in enhancing the biological activity of innate immune cells and in treating allergy and caner (in particular colorectal cancer, breast cancer, lung cancer, and lymphoma).

SUMMARY

Therefore, in a first aspect, the present disclosure provides a refined product obtained from a rice hull. The refined product is produced by a process which comprises the steps of:

subjecting a rice hull to extraction with an aqueous solution so as to obtain an aqueous extract, admixing the aqueous extract with a first alcohol so as to obtain a first precipitate, subjecting the first precipitate to an enzymatic hydrolysis treatment so as to obtain an aqueous enzymatic hydrolysate, the enzymatic hydrolysis treatment employing an aqueous composition containing α-amylase, protease, and amyloglucosidase, admixing the aqueous enzymatic hydrolysate with a second alcohol so as to obtain a second precipitate, and refining the second precipitate by anion exchange chromatography, such that the refined product thus obtained consists essentially of a type II arabinogalactan having a number average molecular weight ranging from 56 to 103 kDa.

In a second aspect, the present disclosure provides a method for enhancing the biological activity of innate immune cells in a subject, which comprises administering to the subject a refined product as described above.

In a third aspect, the present disclosure provides a method for treating a subject having or suspected of having allergy, which comprises administering to the subject a refined product as described above.

In a fourth aspect, the present disclosure provides a method for treating a subject having or suspected of having cancer, which comprises administering to the subject a refined product as described above.

In a fifth aspect, the present disclosure provides a process for producing a refined product from a rice hull, which comprises:

subjecting a rice hull to extraction with an aqueous solution so as to obtain an aqueous extract, admixing the aqueous extract with a first alcohol so as to obtain a first precipitate, subjecting the first precipitate to an enzymatic hydrolysis treatment so as to obtain an aqueous enzymatic hydrolysate, the enzymatic hydrolysis treatment employing an aqueous composition containing α-amylase, protease, and amyloglucosidase, admixing the aqueous enzymatic hydrolysate with a second alcohol so as to obtain a second precipitate, and refining the second precipitate by anion exchange chromatography, such that the refined product thus obtained consists essentially of a type II arabinogalactan having a number average molecular weight in the range of 56 to 103 kDa.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which.

DETAILED DESCRIPTION

Figure 1:
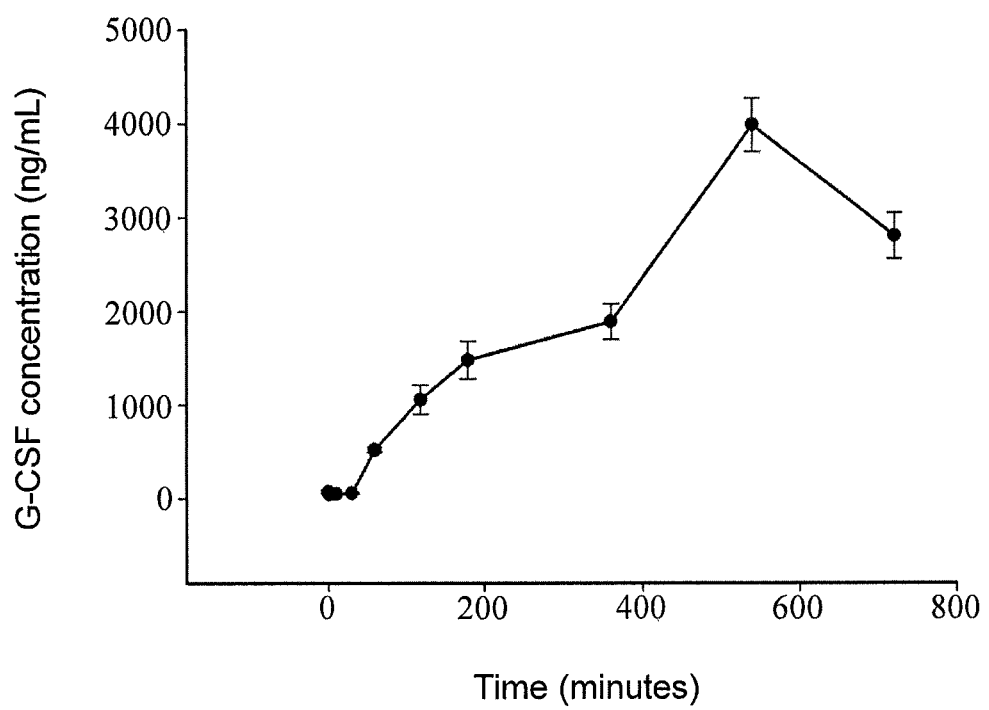
FIG. 1 shows the effect of the refined product of the present disclosure upon the G-CSF concentration of mouse serum.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

In order to design a novel drug effective in improving the biological activity of innate immune cells and in treating allergy and cancer, the inventor attempted to subject a rice hull to extraction with an aqueous solution. The thus obtained aqueous extract was subsequently subjected to precipitation, enzymatic hydrolysis, and refinement, such that a refined product from the rice hull was obtained. The refined product consists essentially of a type II arabinogalactan having a number average molecular weight in the range of 56 to 103 kDa.

Therefore, the present disclosure provides a refined product obtained from a rice hull. The refined product is produced by a process which comprises the steps of:

subjecting a rice hull to extraction with an aqueous solution so as to obtain an aqueous extract, admixing the aqueous extract with a first alcohol so as to obtain a first precipitate, subjecting the first precipitate to an enzymatic hydrolysis treatment so as to obtain an aqueous enzymatic hydrolysate, the enzymatic hydrolysis treatment employing an aqueous composition containing α-amylase, protease, and amyloglucosidase, admixing the aqueous enzymatic hydrolysate with a second alcohol so as to obtain a second precipitate, and refining the second precipitate by anion exchange chromatography, so that the refined product thus obtained consists essentially of a type II arabinogalactan having a number average molecular weight in the range of 56 to 103 kDa.

As used herein, the term "refined product" refers to a purified substance free of impurities, which is obtained by subjecting a raw material to purification, processing, separation, and/or concentration.

As used herein, the terms "rice hull" and "rice husk" can be used interchangeably.

As used herein, the term "number average molecular weight" refers to a molecular weight that is determined by dividing the total weight of all the polymer molecules in a sample with the total number of the polymer molecules in the sample. In an exemplary embodiment of the present disclosure, the type II arabinogalactan in the refined product has a number average molecular weight of 77 kDa.

According to the present disclosure, the step of subjecting a rice hull to extraction with an aqueous solution can be carried out by virtue of techniques well-known in the art and commonly used. In this regard, reference can be made to, for example, Esther Marie Goellner et al. (2011), supra, TW I379688 B1, and Yang L. C. et al. (2013), supra.

It is understandable that the operation condition for the extraction step should vary with the ratio of the aqueous solution to the rice hull so as to provide an optimal extraction effect. One skilled in the art can readily determine the suitable operation condition for the extraction step.

According to the present disclosure, the rice hull to be used may be obtained from a rice plant selected from *Oryza sativa, Oryza officinalis, Oryza nivara, Oryza rufipogon, Oryza punctata, Oryza glaberrima, Oryza australiensis, Oryza barthii, Oryza latifolia, Oryza longistaminata, Oryza meridionalis, Oryza brachyantha, Oryza eichingeri, Oryza grandiglumis,* and *Oryza minuta*. In an exemplary embodiment of the present disclosure, the rice hull to be used is a rice hull of *Oryza sativa*.

According to the present disclosure, the type II arabinogalactan in the refined product is substantially free of 3,6-linked galactose residues.

As used herein, the phrase "substantially free of" means that the recited component is present at an inconsequential level. The recited component may be completely absent, or may be present in an amount that has no measurable effect on the properties of the composition containing the same.

According to the present disclosure, the type II arabinogalactan in the refined product comprises, based on the total amount of galactose residues, 1,3-linked galactose residues in an amount not less than 84.4%.

According to the present disclosure, the type II arabinogalactan in the refined product comprises, based on the total amount of galactose residues, 1,6-linked galactose residues in an amount ranging from 1.6% to 4% and terminally linked galactose residues in an amount ranging from 4% to 15%.

According to the present disclosure, the type II arabinogalactan in the refined product may further comprise 2,4-linked glucose residues, 3,4-linked glucose residues, 1,2-linked arabinose residues, 4,6-linked mannose residues, terminally linked glucose residues, terminally linked arabinose residues, and terminally linked mannose residues.

According to the present disclosure, the type II arabinogalactan in the refined product may have a molar ratio of galactose residues to arabinose residues which ranges from about 3:1 to about 6:1. In an exemplary embodiment of the present disclosure, the type II arabinogalactan in the refined product has a molar ratio of galactose residues to arabinose residues being 4.48:1.

According to the present disclosure, the first and second alcohols used in the preparation process of the refined product may be identical or different, and are selected from the group consisting of methanol, ethanol, propanol, and combinations thereof. In an exemplary embodiment of the present disclosure, each of the first and second alcohols used in the preparation process of the refined product is ethanol.

By virtue of in vitro cell study and in vivo animal testing, It has been verified that the refined product obtained from a rice hull according to the present disclosure is able to effectively enhance the biological activity of innate immune cells, and has a therapeutic effect on allergy and cancer (in particular colorectal cancer, breast cancer, lung cancer, and lymphoma).

Therefore, the present disclosure provides a pharmaceutical composition for enhancing the biological activity of innate immune cells, which comprises a refined product obtained from a rice hull as described above.

According to the present disclosure, the innate immune cells to be treated are selected from the group consisting of macrophages, neutrophils, natural killer cells, and combinations thereof.

The present disclosure also provides a pharmaceutical composition for treating allergy, which comprises a refined product obtained from a rice hull as described above.

As used herein, the terms "treating" and "treatment" refer to preventing, reducing, alleviating, ameliorating, relieving, or controlling one or more clinical signs of a disease or disorder; and mean lowering, stopping, or reversing the progression or severity of a condition or symptom being treated.

As used herein, the term "allergy" refers to a hypersensitivity reaction induced by the immune system in response to a specific allergen, which might lead to an adverse symptom.

As used herein, the terms "allergy" and "hypersensitivity" can be interchangeably used.

According to the present disclosure, types of the allergy to be treated include, but are not limited to, IgE-mediated immediate hypersensitivity (i.e. type I hypersensitivity), IgG or IgM-mediated cytotoxic hypersensitivity (i.e. type II hypersensitivity), immune complex-mediated hypersensitivity (i.e. type III hypersensitivity), and T cell-mediated delayed hypersensitivity (i.e. type IV hypersensitivity). In an exemplary embodiment of the present disclosure, the allergy to be treated is IgE-mediated immediate hypersensitivity.

The present disclosure also provides a pharmaceutical composition for treating cancer, which comprises a refined product obtained from a rice hull as described above.

According to the present disclosure, the cancer to be treated is selected from the group consisting of colorectal cancer, breast cancer, lung cancer, lymphoma, and combinations thereof.

The pharmaceutical composition according to the present disclosure can be formulated into a dosage form suitable for parenteral or oral administration using technology well known to those skilled in the art, which includes, but is not limited to, injections (e.g., sterile aqueous solutions or dispersions), sterile powders, tablets, troches, lozenges, pills, capsules, dispersible powders or granules, solutions, suspensions, emulsions, syrups, elixirs, slurries, and the like.

The pharmaceutical composition according to the present disclosure can additionally comprise a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of these agents are within the expertise of those skilled in the art.

The pharmaceutical composition according to the present disclosure may comprise a pharmaceutically acceptable solvent selected from the group consisting of water, normal saline, phosphate buffered saline (PBS), sugar-containing solutions, aqueous solutions containing an alcohol, and combinations thereof. In an exemplary embodiment of the present disclosure, the pharmaceutically acceptable solvent is PBS.

The pharmaceutical composition according to the present disclosure may be administered via a parenteral route selected from the group consisting of intraperitoneal injection, subcutaneous injection, intramuscular injection, and intravenous injection. In an exemplary embodiment of the present disclosure, the pharmaceutical composition is formulated into a dosage form suitable for intraperitoneal injection. In another exemplary embodiment of the present disclosure, the pharmaceutical composition is formulated into a dosage form suitable for intravenous injection.

The present disclosure also provides a method for enhancing the biological activity of innate immune cells in a subject, which comprises administering to the subject a refined product as described above. In an exemplary embodiment of the present disclosure, the aforesaid pharmaceutical composition for enhancing the biological activity of innate immune cells is administered to the subject.

As used herein, the terms "administering" and "administration" can be interchangeably used.

The present disclosure also provides a method for treating a subject having or suspected of having allergy, which comprises administering to the subject a refined product as described above. In an exemplary embodiment of the present disclosure, the aforesaid pharmaceutical composition for treating allergy is administered to the subject.

The present disclosure also provides a method for treating a subject having or suspected of having cancer, which comprises administering to the subject a refined product as described above. In an exemplary embodiment of the present disclosure, the aforesaid pharmaceutical composition for treating cancer is administered to the subject.

The dosage and the frequency of administration of the refined product obtained from a rice hull according to the present disclosure may vary depending on the following factors: the severity of the disease to be treated, the route of administration, and the weight, age, physical condition and response of the subject to be treated. Generally speaking, the pharmaceutical composition according to the present disclosure may be orally or parenterally administered in a single dose or in several doses.

The present disclosure will be further described by way of the following examples. However, it should be understood that the following examples are solely intended for the purpose of illustration and should not be construed as limiting the present disclosure in practice.

EXAMPLES

Experimental Materials:
1. Source and Cultivation of Cell Lines

The following cell lines used in the examples were all purchased from the Bioresource Collection and Research Center of the Food Industry Research and Development Institute (BCRC of FIRDI, Taiwan): mouse macrophage cell line RAW 264.7 (ATCC TIB-71; BCRC 60001), mouse lymphoma cell line YAC-1 (ATCC TIB-160; BCRC 60147), mouse colon carcinoma cell line CT26 (ATCC CRL-2369; BCRC 60443), human lung carcinoma cell line A549 (ATCC CCL-185; BCRC 60074), human breast cancer cell line MDA-MB-231 (ATCC HTB-26; BCRC 60425), and human natural killer cell line NK-92MI (ATCC CRL-2408; BCRC 60438).

The cells of each of the aforesaid six cell lines were cultivated using a respective medium shown in Table 1 and a 10-cm Petri dish in an incubator (37° C. and 5% $CO_2$). Medium change was performed approximately every three days. When about 80-90% confluence was reached, medium removal was conducted, followed by washing the cells two times with PBS (pH 7.4; Amresco, USA). Trypsin-EDTA was added so as to detach the cells from the bottom of the Petri dish. Subsequently, a fresh medium was added to neutralize the activity of the trypsin, and the cells were sufficiently dispersed by virtue of repeated aspiration with a pipette. The resultant cell suspension was transferred to a flask, followed by cultivation in an incubator.

TABLE 1

| Cell line | Medium |
|---|---|
| RAW 264.7 and CT26 | Dulbecco's Modified Eagle's Medium (DMEM)(Hyclone) supplemented with 10% fetal bovine serum (FBS)(Gibco), 100 IU/mL penicillin, and 100 μg/mL streptomycin |

TABLE 1-continued

| Cell line | Medium |
| --- | --- |
| YAC-1 | RPMI 1640 medium (Hyclone) supplemented with 2 mM L-glutamine (Biological Inc.), 1.5 g/L sodium bicarbonate (Sigma Aldrich), 4.5 g/L glucose, 10 mM HEPES (Biological Inc.), 1 mM sodium pyruvate (Biological Inc.), and 10% FBS |
| A549 | Ham's F12 medium supplemented with 2 mM L-glutamine, 1.5 g/L sodium bicarbonate, and 10% FBS |
| MDA-MB-231 | Leibovitz's L-15 medium supplemented with 2 mM L-glutamine and 10% FBS |
| NK-92MI | Alpha-minimum essential medium (α-MEM) supplemented with 2 mM L-glutamine, 1.5 g/L sodium bicarbonate, 0.2 mM inositol (Gibco), and 0.1 mM 2-mercaptoethanol (Biological Inc.) |

2. Experimental Animals

The male ICR (imprinting control region) mice (8 to 10 weeks of age, a body weight of about 30 g) and male BALB/c mice (8 to 10 weeks of age, a body weight of about 26 g) used in the examples were all purchased from National Laboratory Animal Center. In accordance with the guidelines approved by National Science Council of Taiwan, all of the experimental animals were raised in an air-conditioned room with the following conditions: a 12 hour light/12 hour dark cycle, 22±2° C., and relative humidity of 60±10%. Furthermore, food and water were provided ad libitum for all of the experimental animals. All of the experimental procedures for animal testing comply with the regulation of Animal Protection Act of Taiwan, and were performed in accordance with the guidelines of the Animal Care Committee of the Council of Agriculture in Taiwan.

General Experimental Procedure:
Statistical Analysis

In the following examples, each group was subjected to the same experiment for 3 times. The experimental data are expressed as mean±standard deviation (S.D.), and were analyzed by virtue of Dunnett's test so as to assess the difference between all the groups. $p<0.05$ indicates a statistically significant difference.

Example 1

Preparation of Refined Product Obtained from Rice Hull of Oryza sativa 100 kg of rice hulls of Tai-Keng No. 9 (a rice plant of Oryza sativa; harvested in 2010 and purchased from Experimental Agriculture Station of National Chung Hsing University, Taichung) were ground, followed by adding 1,500 L of deionized water and heating at 100° C. for 3 hours. Filtration and concentration under a reduced pressure were conducted to obtain 100 L of an aqueous extract. Subsequently, 400 L of 95% ethanol was added to the aqueous extract, and the resultant mixture was left standing at 4° C. for 16 hours. The thus formed precipitate was collected, and was subjected to an enzymatic hydrolysis treatment at 95° C. for 1.5 hours so that the proteins and starches in the precipitate were hydrolyzed. Specifically, the enzymatic hydrolysis treatment was conducted using 50 μL of α-amylase (3,000 U/mL)(Megazyme, Cat. No. E-BLAAM), 100 μL of a protease (300 U/mL)(Megazyme, Cat. No. E-BSPRT), and 200 μL of amyloglucosidase (3,300 U/mL) (Megazyme, Cat. No. E-AMGDF) per gram of the precipitate. Afterward, ethanol precipitation was performed using 200 mL of 95% ethanol for 12 hours. The resultant supernatant was removed, and the remaining precipitate was dissolved in deionized water, followed by performing a refinement treatment with an affinity column (TOYOPEARL® DEAE-650M) containing an anion exchange resin so as to obtain a liquid eluate in yellow color. Subsequently, the eluate was dried in an oven at a temperature of 60° C. Therefore, a refined product in dry powder form was obtained.

Example 2

Characterization of Refined Product Obtained from Rice Hull of Oryza sativa

In order to investigate the physicochemical properties of the refined product obtained from a rice hull of Oryza sativa according to the present disclosure, the refined product prepared in Example 1 was used for the following experiments.

A. Determination of Protein Content 10 mg of the refined product prepared in Example 1 was dissolved in 1 mL of deionized water, followed by evenly mixing to obtain an aqueous mixture. 10 μL of the aqueous mixture was used as a test sample and was mixed with 90 μL of CB-protein assay reagent (G-Biosciences, Cat. No. #786-012). Subsequently, the resultant mixture was placed into a microplate and was left standing at room temperature for 10 minutes. The absorbance at 570 nm ($OD_{570}$) was measured using a microplate reader.

Furthermore, bovine serum albumin (BSA) standards were subjected to the same experiment. The protein content in the refined product was calculated using a standard curve prepared by plotting different known BSA concentrations versus their respective $OD_{570}$ values. The results indicate that the refined product obtained from a rice hull of Oryza sativa contains no protein.

B. Molecular Weight Determination

This experiment was performed by virtue of high-performance size-exclusion chromatography (HPSEC). The instruments and operating conditions for HPSEC are shown in Table 2.

TABLE 2

| | |
| --- | --- |
| Column | TSK guard column PWH (75 × 7.5 mm; TOSOH), TSK G4000PWxl column (300 × 7.8 mm; TOSOH), and TSK G2500PWxl column (300 × 7.8 mm; TOSOH) |
| Column temperature | 70° C. |
| Detector | Refractive index detector (Wyatt) |
| Detector temperature | 35° C. |
| Eluent | 0.3N sodium nitrate solution containing 0.02% (w/w) sodium azide |
| Flow rate (mL/minute) | 0.8 |

1 mg of the refined product prepared in Example 1 was dissolved in 1 mL of the eluent shown in Table 2, followed by filtration with a filter membrane having a pore size of 0.45 μm. Then, 20 μL of the resultant filtrate was used as a test sample and was subjected to HPSEC, and the retention times of peaks in the chromatography profile thus obtained were recorded. Additionally, pullulan standards were subjected to the same experiment. A calibration line was constructed by plotting the log values of the molecular weights of the pullulan standards versus their respective retention times, and the number average molecular weight of the refined product was determined based on the data above.

By virtue of HPSEC, the refined product was determined to have a number average molecular weight of 77 kDa.

In addition, the inventor prepared more refined products from rice hulls of Oryza sativa harvested in different years (2011 and 2012) according to the method described in Example 1, and determined their molecular weights according to the method described in the present section. The results manifest that the refined product obtained from the rice hull of Oryza sativa harvested in 2011 has a number average molecular weight of 56 kDa, and the refined product obtained from the rice hull of Oryza sativa harvested in 2012 has a number average molecular weight of 103 kDa.

C. Analysis of Monosaccharide Content

This experiment was performed using a high-performance anion-exchange chromatography (HPAEC) system with a pulsed amperometric detector (Wyatt, USA). The instruments and operating conditions for HPAEC are shown in Table 3.

TABLE 3

| Column | CarboPac PA1 column (Dionex) |
|---|---|
| Column length | 250 mm |
| Column internal diameter | 4 mm |
| Eluent | 10 mM sodium hydroxide and 1 mM barium acetate |
| Flow rate (mL/minute) | 1 |

10 mg of the refined product prepared in Example 1 was dissolved in 4 mL of a 2 M trifluoroacetic acid solution, followed by hydrolysis at 100° C. for 4 hours. The resultant hydrolysate was heated at 50° C. for 40 minutes, and the eluent shown in Table 3 was subsequently added to reach a final concentration of 50 μg/mL. 20 μL of the resultant hydrolysate solution was used as a test sample and was subjected to HPAEC analysis, and the area of each peak in the chromatography profile thus obtained was calculated.

Additionally, for the purpose of comparison, an aqueous mixture containing arabinose, galactose, glucose, mannose, and xylose was used as a standard and was subjected to the same experiment. The area of each peak in the chromatography profile thus obtained was calculated and was used for the comparison. The monosaccharide content of the refined product was determined via the comparison.

The results based on HPAEC reveal that amongst the monosaccharide components contained in the refined product, galactose is present in the highest amount (44.8 mol %), sequentially followed by glucose (29.8 mol %), arabinose (10 mol %), mannose (9.3 mol %), and xylose (6.1 mol %).

D. Linkage Analysis

This experiment was performed by virtue of gas chromatography-mass spectrometry (GC-MS), specifically, using the following instruments: a GC-MS system (Agilent) and a column (DB5, length: 30 m, internal diameter: 0.25 mm, OV-1701, Agilent) equipped with a film having a thickness of 0.2 μm. The operating conditions of GC-MS are shown in Table 4.

TABLE 4

| Temperature rising procedure for column oven | The temperature is maintained at 100° C. for 2 minutes, is risen to 180° C. (at a rate of 8° C./minute) and maintained thereat for 2 minutes, and is risen to 240° C. (at a rate of 2° C./minute) and maintained thereat for 5 minutes. |
|---|---|
| Carrier gas | Helium |
| Flow rate of carrier gas | 1 mL/minute |
| Injector temperature | 260° C. |
| Detector temperature | 300° C. |
| Injection volume of sample | 1 μL |
| Electron ionization (EI) mode of mass spectrometer | 70 eV |

The linkage analysis was conducted substantially according to the method described in Carpita and Shea (1989), Chapter 9: Analysis of Carbohydrates by GLC and MS., eds Chritopher J. Biermann and Gary D. McGinnis (CRC Press, USA), except for minor modifications. Briefly, the refined product prepared in Example 1 was dissolved in 500 μL of DMSO. Subsequently, the carboxyl groups and the hydroxyl groups of the polysaccharide molecules in the resultant refined product solution were subjected to methylation according to the partially methylated alditol acetates (PMAA) derivation method described in Carpita and Shea (1989), supra. A drying process was performed, and 3 mg of the resultant powder was dissolved in 250 μL of 2 N trifluoroacetic acid solution, followed by hydrolysis at 121° C. for 1 hour. The resultant hydrolysate was dried using a nitrogen blowing instrument (Thermal), and 2 mL of isopropanol was added so as to remove the trifluoroacetic acid solution. Then, 250 μL of ammonium hydroxide was added to the dried hydrolysate product, followed by stirring. 500 μL of a sodium borodeuteride solution was added, and the reaction was allowed to proceed at 40° C. for 90 minutes. The resultant reaction product was subjected to acetylation using 500 μL of acetic anhydride, followed by washing with 4 mL of dichloromethane and 2 mL of sterilized water. A drying process was conducted using the aforesaid nitrogen blowing instrument, and 1 mL of acetone was added. The sample thus obtained was injected into the GC-MS system for analysis. Afterward, the result was subjected to comparison with the mass spectrum of known compounds available in the database provided by the Complex Carbohydrate Research Center (The University of Georgia, Athens, Ga., USA) so as to analyze the linkage between the monosaccharide residues in the refined product.

The results of linkage analysis for the refined product based on SC-MS are shown in Table 5. Among the monosaccharide components of the refined product, most of galactose residues exist as 1,3-linked galactose and form a linear chain. The refined product has no 1,4-linked galactose residue. Therefore, it is indicated that the refined product is a type II arabinogalactan. Additionally, it is revealed that the refined product contains branched chains of 4,6-linked mannose residues, 2,4-linked glucose residues and 3,4-linked glucose residues, as well as terminally linked arabinose residues, terminally linked mannose residues, terminally linked glucose residues and terminally linked galactose residues.

TABLE 5

| monosaccharide component | Linkage | Molar percentage (mol %) |
|---|---|---|
| Arabinose | Terminal | 5.1 |
| | 1,2- | 4.9 |
| Mannose | Terminal | 4.6 |
| | 4,6- | 4.7 |
| Glucose | Terminal | 9.6 |
| | 3,4- | 8 |
| | 2,4- | 12.2 |
| Galactose | Terminal | 1.8 |
| | 1,3- | 42.3 |
| | 1,6- | 0.7 |
| Others | — | 6.1 |

In addition, in order to verify that the refined product of the present disclosure differs from known type II arabinogalactans obtained from other biosources, the inventor compared the source, monosaccharide content, and linkage of monosaccharides regarding the refined product of the present disclosure with those regarding the type II arabinogalactans disclosed in Table 2 of WO 2011/139168 A1 (hereinafter referred to as D1), Birgit Classen et al. (2000), supra (hereinafter referred to as D2), Esther Marie Goellner et al. (2011), supra (hereinafter referred to as D3), and Yang L. C. et al. (2014), supra (hereinafter referred to as D4). The monosaccharide content and linkage of monosaccharides regarding the refined product of the present disclosure were determined in sections C and D of this example. The comparison is shown in Table 6.

TABLE 6

| | Source | Molar ratio of galactose residues to arabinose residues | Major galactose residues |
|---|---|---|---|
| Refined product of present disclosure | rice hull of *Oryza sativa* | 4.48:1 | 1,3-linked galactose residues |
| type II arabinogalactan of D1 | honey | 0.84:1 to 1.27:1 | 3,6-linked galactose residues |
| type II arabinogalactan of D2 | *Echinacea purpurea* | 1.8:1 | 3,6-linked galactose residues |
| type II arabinogalactan of D3 | *Larix laricina* | 6:1 | 3,6-linked galactose residues |
| type II arabinogalactan of D4 | *Anoectochilus formosanus* | 2.53:1 | 3,6-linked galactose residues |

As shown in Table 6, the source, molar ratio of galactose residues to arabinose residues, and major linkage type of galactose residues regarding the refined product of the present disclosure are all different from those regarding the type II arabinogalactans disclosed in the aforesaid prior art documents. In particular, most galactose residues of the type II arabinogalactans disclosed in D1 to D4 exist as 3,6-linked galactose residues and form a branched chain. By contrast, according to the results shown in Table 5, the refined product of the present disclosure contains no 3,6-linked galactose residue. In view of the foregoing, the inventor opines that the refined product of the present disclosure is a novel type II arabinogalactan.

Example 3

Evaluation for Enhancing Effect of Refined Product of Present Disclosure Upon Biological Activity of Innate Immune Cells In order to investigate whether the refined product of the present disclosure can effectively enhance the concentration of granulocyte-colony stimulating factor (G-CSF) and tumor necrosis factor-α (TNF-α; a cytokine serving as an indicator at the early stage of immune response) to further improve the biological activity of innate immune cells (such as macrophages, neutrophils, and natural killer cells), the refined product prepared in Example 1 was employed in the following experiments.

A. Determination of G-CSF Concentration and TNF-α Concentration in ICR Mouse Serum The refined product prepared in Example 1 was dissolved in PBS (pH 7.4), followed by intravenously injecting the resultant refined product solution into each of 27 male ICR mice via the tail vein (at a dose of 15 mg/kg). 1, 10, 30, 60, 120, 180, 360, 540, and 720 minutes after the injection, blood was collected from the vein in the abdominal cavity of each mouse. Subsequently, centrifugation was conducted at 4° C. and 4700 rpm for 10 minutes so as to obtain a serum sample. The G-CSF concentration and TNF-α concentration in the serum sample were determined using murine G-CSF standard ELISA development kit (Preprotech., Cat. No. 900-k103, N.J., USA) and murine TNF-α kit (eBioscience, Cat. No. 88-7324, C.A., USA) according to the instructions provided by the manufacturer.

Figure 2:
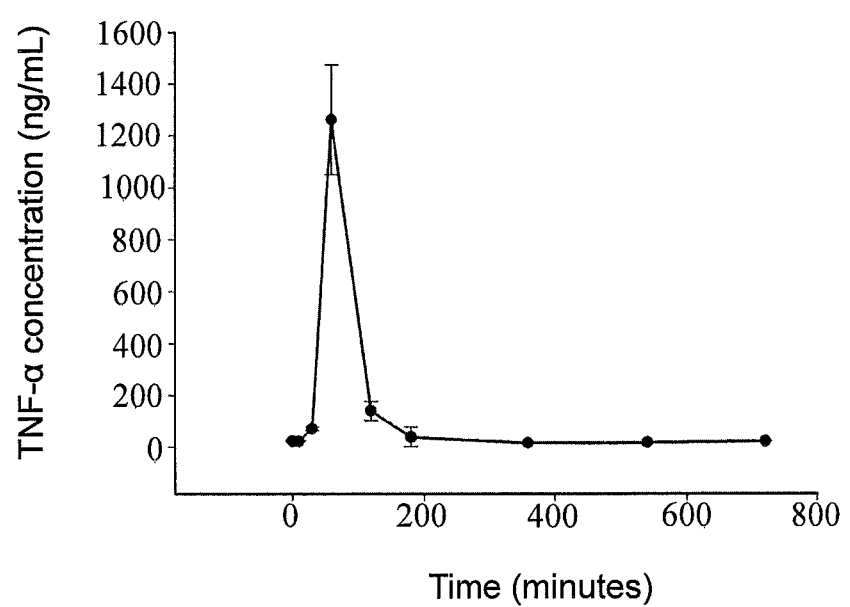
FIG. 2 shows the effect of the refined product of the present disclosure upon the TNF-α concentration of mouse serum.

FIGS. 1 and 2 respectively show the effects of the refined product of the present disclosure upon the G-CSF concentration and TNF-α concentration in mouse serum.

As shown in FIG. 1, after the intravenous injection with the refined product of the present disclosure, the G-CSF concentration in the serum of the ICR mice increased with time. Particularly, 540 minutes after the intravenous injection, the G-CSF concentration in the serum of the ICR mice reached the highest level. As shown in FIG. 2, 60 minutes after the intravenous injection with the refined product of the present disclosure, the TNF-α concentration in the serum of the ICR mice reached the highest level. The aforesaid results indicate that the refined product of the present disclosure can increase the G-CSF concentration in serum for a long period and rapidly increase the TNF-α concentration in serum, thereby being able to enhance the biological activity of innate immune cells.

In view of the foregoing, the inventor used the refined product of the present disclosure in the following experiments, so as to verify that the refined product of the present disclosure is able to effectively enhance the biological activity of innate immune cells.

B. Determination of Nitrite Concentration of RAW 264.7 Macrophages

The experiment set forth in this section was performed in order to investigate whether the refined product of the present disclosure is effective in stimulating the activity of macrophages, and whether the refined product of the present disclosure is superior to type II arabinogalactans obtained from other biological materials in terms of the stimulation effect.

First of all, the inventor prepared a refined product from a rice bran of *Oryza sativa* substantially according to the method described in Example 1, except that a rice bran was used as the biological material for extraction instead of a rice hull. The inventor also used the type II arabinogalactan disclosed in Yang L. Q. et al. (2014), supra (hereinafter referred to as the refined product from *Anoectochilus formosanus*) in the experiment set forth in this section. Specifically, each of the refined product from *Anoectochilus formosanus*, the refined product from a rice bran of *Oryza sativa*, and the refined product prepared in Example 1 was dissolved in PBS (pH 7.4), so that three refined product solutions having a concentration of 1000 μg/mL (hereinafter referred to as refined product solutions 1 to 3, respectively) were obtained.

Five groups of RAW 264.7 cells (i.e. a control group, a positive control group, and three experimental groups referred to as Experimental Groups 1 to 3), which were prepared via subculturing according to section 1 of "Experimental Materials", were provided. The cells in each group were cultivated using 100 μL of DMEM (supplemented with 10% FBS, 100 IU/mL penicillin, and 100 μg/mL streptomycin) in a 96-well plate at $3\times10^5$ cells/well, and the cultivation was conducted in an incubator (37° C., 5% $CO_2$) for 24 hours.

Refined product solutions 1 to 3 in a suitable amount were respectively added to the cultures of Experimental Groups 1 to 3, so that the final concentration of the refined product in the culture of each of Experimental Groups 1 to 3 was 100 μg/mL. Moreover, a suitable amount of a lipopolysaccharide (LPS)(Sigma Aldrich) was added to the culture of the positive control group, so that the final concentration of LPS in the culture of the positive control group was 1 μg/mL. 100 μL of DMEM was added to the culture of the control group. Afterward, cultivation was performed in an incubator (37° C., 5% $CO_2$) for 24 hours. The resultant culture supernatant was collected, and was added into the respective well of a microplate at 100 μL/well. Subsequently, 100 μL of Griess reagent (Sigma Aldrich) was added into the respective well, and the reaction was allowed to proceed at room temperature for 15 minutes. $OD_{570}$ (the absorbance at 570 nm) of the respective well was measured using a microplate reader (Dynex Technologies, USA). The $OD_{570}$ value thus obtained was converted to a nitrite concentration (μM) according to a standard curve constructed by plotting different known concentrations of sodium nitrite ($NaNO_2$) and their $OD_{570}$ values.

Figure 3:
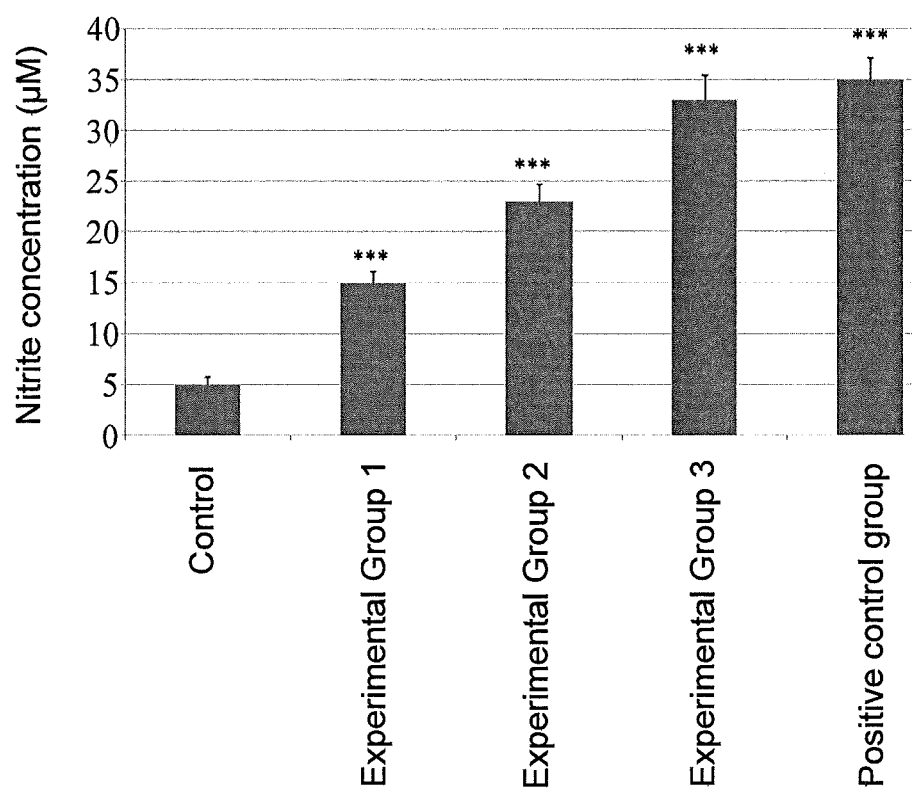
FIG. 3 shows the effects of the refined products obtained from different biological materials upon the nitrite concentration of RAW 264.7 cells, wherein RAW 264.7 cells in the control group were treated with DMEM, RAW 264.7 cells in Experimental Group 1 were treated with a type II arabinogalactan obtained from *Anoectochilus formosanus* (at a concentration of 100 μg/mL), RAW 264.7 cells in Experimental Group 2 were treated with a type II arabinogalactan obtained from a rice bran of *Oryza sativa* (at a concentration of 100 μg/mL), RAW 264.7 cells in Experimental Group 3 were treated with the refined product of the present disclosure (at a concentration of 100 μg/mL), RAW 264.7 cells in the positive control group were treated with a lipopolysaccharide (at a concentration of 1 μg/mL), and "***" indicates $p<0.001$ when compared to the control group.

FIG. 3 shows the effects of the refined products obtained from different biological materials upon the nitrite concentration of RAW 264.7 cells. As shown in FIG. 3, compared to the control group, the nitrite concentration of each of Experimental Groups 1 to 3 is higher. Particularly, the nitrite concentration of Experimental Group 3 is similar to that of the positive control group, and is higher than that of each of Experimental Groups 1 and 2. The abovementioned results manifest that the refined product of the present disclosure can effectively increase the nitrite concentration of RAW 264.7 macrophages, and hence has a stimulation effect on the activity of macrophages, and that the refined product of the present disclosure is superior to the refined products obtained from a rice bran of *Oryza sativa* and *Anoectochilus formosanus* in terms of the effect.

C. Analysis for Phagocytic Capacity of RAW 264.7 Macrophages

Four groups of RAW 264.7 cells (i.e. a control group and three experimental groups referred to as Experimental Groups 1 to 3), which were prepared via subculturing according to section 1 of "Experimental Materials", were provided. The cells in each group were cultivated using 100 μL of DMEM (supplemented with 10% FBS, 100 IU/mL penicillin, and 100 μg/mL streptomycin) in a 96-well plate at $1\times10^5$ cells/well, and the cultivation was conducted in an incubator (37° C., 5% $CO_2$) for 24 hours.

Subsequently, a suitable amount of the refined product solution obtained according to section A of this example was added to the culture of each of Experimental Groups 1 to 3, so that the final concentrations of the refined product of the present disclosure in the cultures of Experimental Groups 1 to 3 were 10 μg/mL, 50 μg/mL, and 100 μg/mL, respectively. The culture of the control group received no treatment. The culture of each group was subjected to cultivation in an incubator (37° C., 5% $CO_2$) for 24 hours, followed by removing the liquid in the respective well. Fluorescein isothiocyanate-labeled *Escherichia coli* cells (Bioparticles®, USA) were added to the resultant culture of each group at $2.5\times10^6$ cells/well. Cultivation was performed in an incubator (37° C., 5% $CO_2$) for 2 hours. Subsequently, $OD_{538}$ (the absorbance at 538 nm) of the respective well was measured using a fluorescence/luminescence plate reader (TRIAD LT, Dynex)($OD_{538}$ thus obtained is referred to as the first absorbance). 100 μL of trypan blue was added to the culture of each group, followed by uniformly mixing. $OD_{538}$ of the respective well was measured ($OD_{538}$ thus acquired is referred to as the second absorbance).

The phagocytic index of each group was calculated using the following formula (I):

$$A=B/C \qquad (I)$$

A: phagocytic index
B: the second absorbance of the respective group
C: the first absorbance of the respective group The data thus obtained were analyzed according to the method described in the "Statistical Analysis" section of "General Experimental Procedure".

Figure 4:
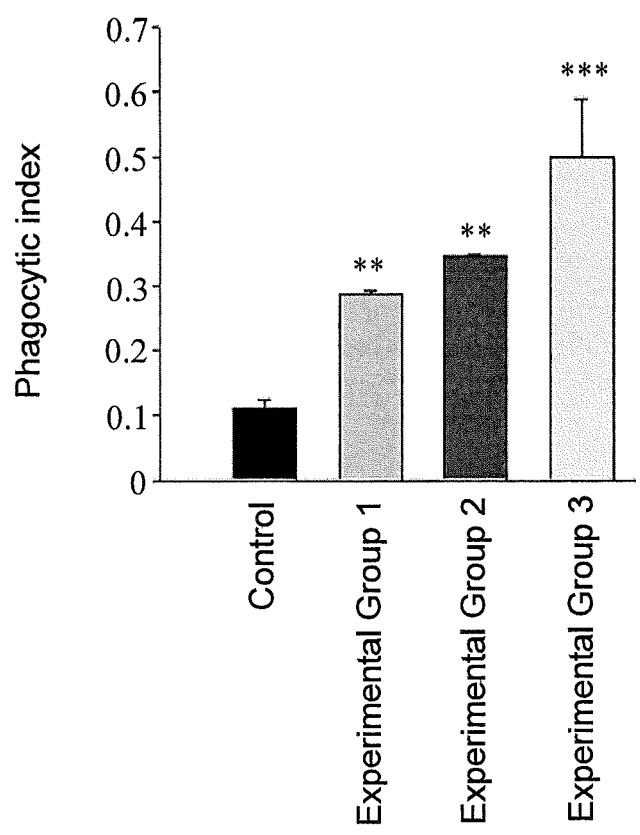
FIG. 4 shows the enhancing effect of the refined product of the present disclosure upon the phagocytic capacity of RAW 264.7 cells, wherein RAW 264.7 cells in the control group received no treatment, RAW 264.7 cells in Experimental Groups 1-3 were treated with the refined product of the present disclosure (respectively at concentrations of 10 μg/mL, 50 μg/mL, and 100 μg/mL), "" indicates $p<0.01$ when compared to the control group, and "*" indicates $p<0.001$ when compared to the control group.

FIG. 4 shows the enhancing effect of the refined product of the present disclosure upon the phagocytic capacity of RAW 264.7 cells. As shown in FIG. 4, the phagocytic index of each of Experimental Groups 1 to 3 is significantly higher than that of the control group, and the enhancement of the phagocytic index becomes more evident when the concentration of the refined product of the present disclosure increases. The aforesaid results reveal that the refined product of the present disclosure is able to effectively enhance the phagocytic activity of macrophages.

D. Analysis for Phagocytic Activity of Macrophages and Neutrophils in Peritoneal Cavity of BALB/c Mice Male BALB/c mice were randomly divided into the following groups (n=10 for each group): a control group and two experimental groups referred to as Experimental Groups 1 and 2. The mice in Experimental Groups 1 and 2 were intraperitoneally injected with the refined product solution prepared in section A of this example respectively at a dose of 3 mg/kg and a dose of 6 mg/kg, and the mice in the control group were intraperitoneally injected with 200 μL of normal saline (the intraperitoneal injection was conducted once a day for two days). On the third day after the beginning of the intraperitoneal injection, the mice in each group were intraperitoneally injected with 100 μL of fluorescein isothiocyanate-labeled *Escherichia coli* cells (in PBS, at a concentration of $1\times10^7$ cells/100 μL). At the end of the first hour after the injection, the mice in each group were sacrificed by virtue of cervical dislocation, followed by sequentially conducting the steps below thrice: (A) injecting 5 mL of PBS into the peritoneal cavity of the respective mouse, (B) gently kneading the peritoneal cavity of the respective mouse so as to mix the fluid therein, and (C) collecting the peritoneal fluid of the respective mouse using a syringe (with a 20 G needle) via abdominal puncture. 15 mL of the peritoneal fluid thus collected was subjected to centrifugation at 4° C. and 300 g for 10 minutes, followed by removing the resultant supernatant. The remaining pellet was subjected to a suspension step using 1 mL of PBS twice so as to prepare a cell suspension. 10 μL of the cell suspension was placed on a hemocytometer, and was subjected to cell counting under an inverted microscope at 100× magnification. 100 μL of the cell suspension was added into a respective well of a 96-well plate at $1\times10^5$ cells/well, followed by adding 100 μL of trypan blue into the respective well. $OD_{535}$ (the absorbance at 535 nm) of the respective well was measured using a fluorescence/luminescence plate reader.

The phagocytic activity of macrophages and neutrophils (%) was determined using the following formula (II):

$$(E/F)\times100 \qquad (II)$$

D: the phagocytic activity of macrophages and neutrophils (%)
E: $OD_{535}$ of the respective group
F: $OD_{535}$ of the control group The data thus obtained were analyzed according to the method described in the "Statistical Analysis" section of "General Experimental Procedure".

Figure 5:
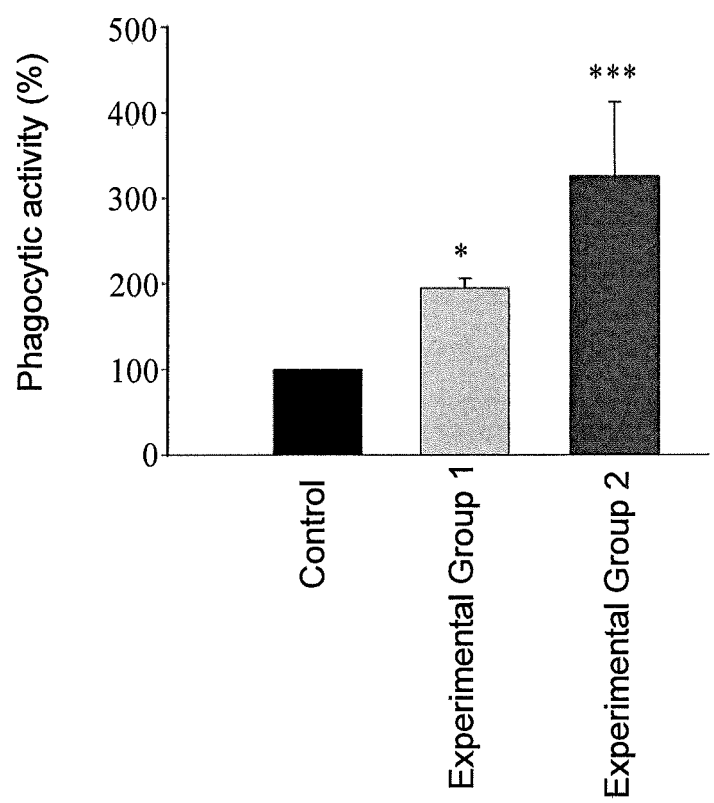
FIG. 5 shows the enhancing effect of the refined product of the present disclosure upon the phagocytic activity of mouse peritoneal macrophages and neutrophils, wherein the BALB/c mice in the control group were injected with normal saline, the BALB/c mice in Experimental Groups 1 and 2 were injected with the refined product of the present disclosure (respectively at doses of 3 mg/kg and 6 mg/kg), "*" indicates $p<0.05$ when compared to the control group, and "***" indicates $p<0.001$ when compared to the control group.

FIG. 5 shows the enhancing effect of the refined product of the present disclosure upon the phagocytic activity of the macrophages and neutrophils in the peritoneal cavity of mice. As shown in FIG. 5, the phagocytic activity of macrophages and neutrophils regarding each of Experimental Groups 1 and 2 is significantly higher than that regarding the control group, and the enhancement of the phagocytic activity of macrophages and neutrophils becomes more evident when the dosage of the refined product of the present disclosure increases. The aforesaid results indicate that the refined product of the present disclosure is able to effectively enhance the in vivo phagocytic activity of macrophages and neutrophils.

E. Analysis for Cytotoxicity of Natural Killer Cells to Lung Cancer Cells and Breast Cancer Cells Five groups of NK-92MI cells (i.e. a control group and four experimental groups referred to as Experimental Groups 1 to 4), which were prepared via subculturing according to section 1 of "Experimental Materials", were provided. For each group, $1 \times 10^6$ cells were cultivated in a 75T flask containing 10 mL of α-MEM [supplemented with 2 mM L-glutamine, 1.5 g/L sodium bicarbonate, 0.2 mM inositol, 0.1 mM 2-mercaptoethanol, 0.02 mM folic acid (Biological Inc.), 12.5% horse serum (Invitrogen), and 12.5% FBS], followed by cultivation in an incubator (37° C., 5% $CO_2$) for 24 hours.

A suitable amount of the refined product solution prepared in section A of this example was added to the culture of each of Experimental Groups 1 to 4, so that the final concentrations of the refined product of the present disclosure in the cultures of Experimental Groups 1 to 4 were 1 μg/mL, 10 μg/mL, 100 μg/mL, and 200 μg/mL, respectively. The culture of the control group received no treatment. After cultivation was performed in an incubator (37° C., 5% $CO_2$) for 12 hours, centrifugation was conducted at 300 g for 10 minutes. The resultant supernatant was removed, and the remaining pellet was subjected to a suspension process using 1 mL of the culture medium so as to prepare a cell suspension. Subsequently, 10 μL of the cell suspension was placed on a hemocytometer, and was subjected to cell counting under an inverted microscope at 100× magnification.

A549 cells, which were prepared via subculturing according to section 1 of "Experimental Materials", were added into a 96-well plate at $1 \times 10^6$ cells/well. Afterward, the cell suspension of the respective group was added at $1 \times 10^6$ cells/well. Co-cultivation was conducted in an incubator (37° C., 5% $CO_2$) for 4 hours. The resultant co-culture was collected and was subjected to centrifugation at 4° C. and 1000 rpm for 10 minutes. Subsequently, 50 μL of the resultant supernatant was obtained and was added into a respective well of a new 96-well plate, and 50 μL of a reaction reagent (Pierce LDH Cytotoxicity Assay Kit, Thermo Scientific) was added into the respective well. The reaction was allowed to proceed at room temperature for 30 minutes. 50 μL of a termination reagent (Pierce LDH Cytotoxicity Assay Kit, Thermo Scientific) was added into the respective well. Afterward, $OD_{490}$ (the absorbance at 490 nm) of each group was measured using a fluorescence/luminescence plate reader.

Furthermore, NK-92MI cells were cultivated using 100 μL of α-MEM (supplemented with 2 mM L-glutamine, 1.5 g/L sodium bicarbonate, 0.2 mM inositol, 0.1 mM 2-mercaptoethanol, 0.02 mM folic acid, 12.5% horse serum, and 12.5% FBS) in a 96-well plate at $1 \times 10^6$ cells/well, followed by cultivation in an incubator (37° C., 5% $CO_2$) for 4 hours. The resultant culture was collected and was subjected to centrifugation at 4° C. and 1000 rpm for 10 minutes. Subsequently, 50 μL of the resultant supernatant was obtained and was added into a respective well of a new 96-well plate, and 50 μL of a reaction reagent was added into the respective well. The reaction was allowed to proceed at room temperature for 30 minutes. 50 μL of a termination reagent was added into the respective well. Afterward, $OD_{490}$ (the absorbance at 490 nm) was measured ($OD_{490}$ thus obtained is referred to as $1^{st}$ comparative absorbance).

In addition, A549 cells were cultivated using 90 μL of Ham's F12 medium (supplemented with 2 mM L-glutamine, 1.5 g/L sodium bicarbonate, and 10% FBS) in a 96-well plate at $1 \times 10^5$ cells/well, followed by cultivation in an incubator (37° C., 5% $CO_2$) for 4 hours. The resultant culture was collected and was subjected to centrifugation at 4° C. and 1000 rpm for 10 minutes. Subsequently, 50 μL of the resultant supernatant was obtained and was added into a respective well of a new 96-well plate, and 50 μL of a reaction reagent was added into the respective well. The reaction was allowed to proceed at room temperature for 30 minutes. 50 μL of a termination reagent was added into the respective well. Afterward, $OD_{490}$ (the absorbance at 490 nm) was measured ($OD_{490}$ thus obtained is referred to as $2^{nd}$ comparative absorbance).

Lastly, additional A549 cells were cultivated using 90 μL of Ham's F12 medium (supplemented with 2 mM L-glutamine, 1.5 g/L sodium bicarbonate, and 10% FBS) in a 96-well plate at $1 \times 10^5$ cells/well, followed by cultivation in an incubator (37° C., 5% $CO_2$) for 4 hours. 10 μL of 10% (w/v) Triton X-100 was added to the resultant culture. Afterward, cell lysis was performed at 37° C. for 10 minutes. The resultant lysate was collected and was subjected to centrifugation at 4° C. and 1000 rpm for 10 minutes. Subsequently, 50 μL of the resultant supernatant was obtained and was added into a respective well of a new 96-well plate, and 50 μL of a reaction reagent was added into the respective well. The reaction was allowed to proceed at room temperature for 30 minutes. 50 μL of a termination reagent was added into the respective well. Afterward, $OD_{490}$ (the absorbance at 490 nm) was measured ($OD_{490}$ thus obtained is referred to as $3^{rd}$ comparative absorbance).

In order to investigate whether the refined product of the present disclosure is effective in enhancing the cytotoxicity of natural killer cells to breast cancer cells, substantially the same experiment as described above was performed, except that MDA-MB-231 cells were used instead of A549 cells.

The percent cytotoxicity of natural killer cells to cancer cells (%) was calculated using the following formula (III):

$$G = (H - I - J)/(K - J) \times 100 \qquad (III)$$

G: the percent cytotoxicity of natural killer cells to cancer cells (%)
H: $OD_{490}$ of the respective group
I: $1^{st}$ comparative absorbance
J: $2^{nd}$ comparative absorbance
K: $3^{rd}$ comparative absorbance The data thus obtained were analyzed according to the method described in the "Statistical Analysis" section of "General Experimental Procedure".

Figure 6:
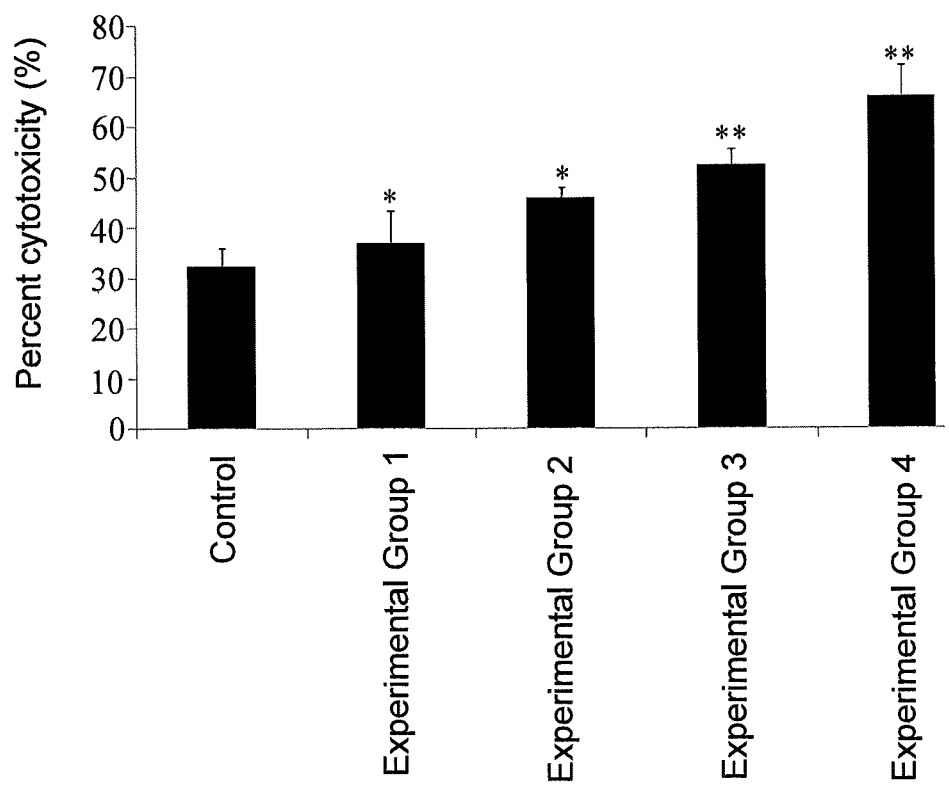
FIG. 6 shows the effect of the refined product of the present disclosure upon the enhancement in the cytotoxicity of natural killer cells to lung cancer cells, wherein NK-92MI cells in the control group were co-cultivated with A-549 cells, NK-92MI cells in Experimental Group 1 were treated with the refined product of the present disclosure (at a concentration of 1 μg/mL) and were co-cultivated with A-549 cells, NK-92MI cells in Experimental Group 2 were treated with the refined product of the present disclosure (at a concentration of 10 μg/mL) and were co-cultivated with A-549 cells, NK-92MI cells in Experimental Group 3 were treated with the refined product of the present disclosure (at a concentration of 100 μg/mL) and were co-cultivated with A-549 cells, NK-92MI cells in Experimental Group 4 were treated with the refined product of the present disclosure (at a concentration of 200 μg/mL) and were co-cultivated with A-549 cells, "*" indicates $p<0.05$ when compared to the control group, and "**" indicates $p<0.01$ when compared to the control group.
Figure 7:
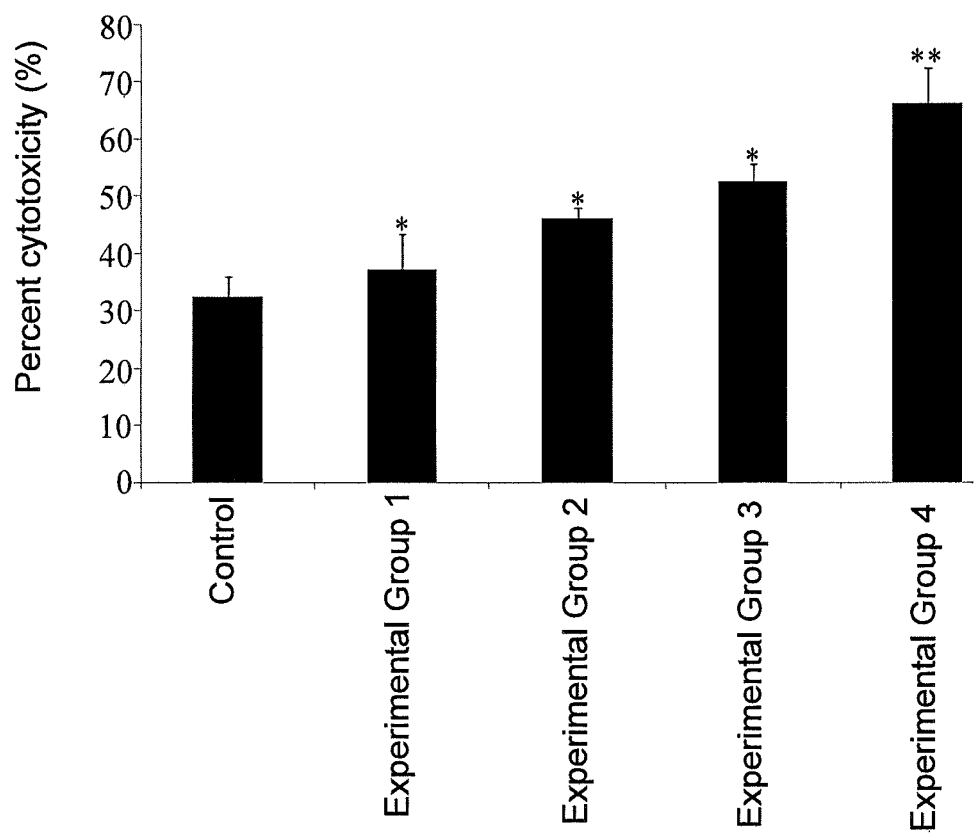
FIG. 7 shows the effect of the refined product of the present disclosure upon the enhancement in the cytotoxicity of natural killer cells to breast cancer cells, wherein NK-92MI cells in the control group were co-cultivated with MDA-MB-231 cells, NK-92MI cells in Experimental Group 1 were treated with the refined product of the present disclosure (at a concentration of 1 μg/mL) and were co-cultivated with MDA-MB-231 cells, NK-92MI cells in Experimental Group 2 were treated with the refined product of the present disclosure (at a concentration of 10 μg/mL) and were co-cultivated with MDA-MB-231 cells, NK-92MI cells in Experimental Group 3 were treated with the refined product of the present disclosure (at a concentration of 100 μg/mL) and were co-cultivated with MDA-MB-231 cells, NK-92MI cells in Experimental Group 4 were treated with the refined product of the present disclosure (at a concentration of 200 μg/mL) and were co-cultivated with MDA-MB-231 cells, "*" indicates $p<0.05$ when compared to the control group, and "**" indicates $p<0.01$ when compared to the control group.

FIGS. 6 and 7 respectively show the effect of the refined product of the present disclosure upon the enhancement in the cytotoxicity of natural killer cells to lung cancer cells and breast cancer cells. As shown in FIGS. 6 and 7, the percent cytotoxicity of each of Experimental Groups 1 to 4 is significantly higher than that of the control group, and the enhancement of the percent cytotoxicity becomes more evident when the concentration of the refined product of the present disclosure increases. The abovementioned results indicate that the refined product of the present disclosure is able to effectively enhance the in vitro cytotoxicity of natural killer cells to lung cancer cells and breast cancer cells.

F. Analysis for Cytotoxicity of Natural Killer Cells in Spleen of BALB/c Mice to Lymphoma Cells Male BALB/c mice were randomly divided into the following groups (n=12 for each group): a control group and three experimental groups referred to as Experimental Groups 1 to 3. The refined product solution prepared in section A of this example was orally administered to the mice in Experimental Groups 1 to 3 (respectively at a dose of 5 mg/kg, a dose of 15 mg/kg, and a dose of 30 mg/kg) once a day for 6 weeks. The mice in the control group received no treatment. At the end of the sixth week of the oral administration, the mice in each group were sacrificed using $CO_2$. Subsequently, the spleen of the mice in each group was collected, and the natural killer cells therein were isolated using a cell strainer (BD Biosciences) with a pore size of 40 μm.

Moreover, YAC-1 cells, which were prepared via subculturing according to section 1 of "Experimental Materials", were cultivated in a 10-cm Petri dish containing RPMI 1640 medium. The cultivation process was conducted in an incubator (37° C., 5% $CO_2$) for 24 hours. 1 mL of the resultant culture of YAC-1 cells ($2\times10^6$ cells/mL) was obtained through suction, followed by adding 15 μL of fluorescent dye BCECF-AM (in DMSO)(Molecular Probes, Cat. No. B1170). The reaction was allowed to proceed at 37° C. for 30 minutes. Subsequently, a washing process was conducted using RPMI 1640 medium so as to remove the fluorescent dye molecules failing to enter the cells. Therefore, fluorescent-labeled YAC-1 cells were obtained.

The fluorescent-labeled YAC-1 cells were added to 25 μL of the natural killer cells of the respective mouse ($2\times10^4$ cells/mL), followed by co-cultivation at 37° C. for 4 hours. The resultant co-culture was collected and was subjected to centrifugation at 4° C. and 800 rpm for 5 minutes. Subsequently, 100 μL of the supernatant thus obtained was added into a 96-well plate. $OD_{538}$ (the absorbance at 538 nm) of each group was measured using a fluorescence/luminescence plate reader (TRIAD LT, Dynex).

In addition, 10 μL of 1% (w/v) Triton X-100 was added to the fluorescent-labeled YAC-1 cells, followed by cell lysis at 37° C. for 30 minutes. The resultant lysate was collected and was added into a 96-well plate. $OD_{538}$ (the absorbance at 538 nm) was measured ($OD_{538}$ thus obtained is referred to as comparative absorbance).

Lastly, a suitable amount of PBS was added into a 96-well plate. Afterward, $OD_{538}$ (the absorbance at 538 nm) was measured ($OD_{538}$ thus obtained is referred to as background absorbance).

The percent cytotoxicity of natural killer cells to lymphoma cells (%) was calculated using the following formula (IV):

$$L=(M-O)/(N-O)\times100 \quad \text{(IV)}$$

L: the percent cytotoxicity of natural killer cells to lymphoma cells (%)
M: $OD_{538}$ of the respective group
N: comparative absorbance
O: background absorbance Table 7 shows the effect of the refined product of the present disclosure upon the enhancement in the cytotoxicity of natural killer cells in the spleen of mice to lymphoma cells. As shown in Table 7, the percent cytotoxicity of each of Experimental Groups 1 to 3 is higher than that of the control group, and the enhancement of the percent cytotoxicity becomes more evident when the dosage of the refined product of the present disclosure increases. The aforesaid results reveal that the refined product of the present disclosure is able to effectively enhance the in vivo cytotoxicity of natural killer cells to lymphoma cells.

TABLE 7

| Group | Dosage of refined product (mg/kg) | Percent cytotoxicity (%) |
|---|---|---|
| Control | — | 13 ± 2.2 |
| Experimental Group 1 | 5 | 17.6 ± 4.9 |
| Experimental Group 2 | 15 | 21 ± 7** |
| Experimental Group 3 | 30 | 24 ± 7*** |

**$p < 0.01$ when compared to the control group
***$p < 0.001$ when compared to the control group Based on the results of sections A to F in this example, the inventor concluded that the refined product of the present disclosure can effectively enhance the biological activity of innate immune cells, thereby being effective against lung cancer, breast cancer, and lymphoma.

Example 4

Evaluation for Anticancer Effect of Refined Product of Present Disclosure on Colon Carcinoma Cells In order to examine whether the refined product of the present disclosure has an anticancer effect on colon carcinoma cells, the refined product prepared in Example 1 was used in the following experiments.

A. Effect of Refined Product of Present Disclosure on Proliferation of Mouse Colon Carcinoma Cells The male BALB/c mice were randomly divided into the following groups (n=8 for each group): a normal control group, a pathological control group, and two experimental groups referred to as Experimental Groups 1 and 2. $1\times10^6$ CT26 cells were subcutaneously injected into the leg of each mouse in the pathological control group and Experimental Groups 1 and 2. The mice in the normal control group received no CT26 cells.

After the injection of CT26 cells, the refined product solution prepared in section A of Example 3 was immediately administered to the mice in Experimental Groups 1 and 2 via intraperitoneal injection respectively at a dose of 5 mg/kg and a dose of 15 mg/kg, and normal saline was administered to the mice in the pathological control group via intraperitoneal injection at a dose of 10 mL/kg. The mice in Experimental Groups 1 and 2 and the pathological control group were subjected to the once-a-day administration until the end of the $3^{rd}$ week after the injection of CT26 cells. The mice in the normal control group received no treatment.

At the end of the $3^{rd}$ week after the injection of CT26 cells, the mice in each group were anesthetized using $CO_2$ and were sacrificed. Then, tumors were collected and weighted. The data thus obtained were analyzed according to the method described in the "Statistical Analysis" section of "General Experimental Procedure". The results are shown in FIG. 8.

Figure 8:
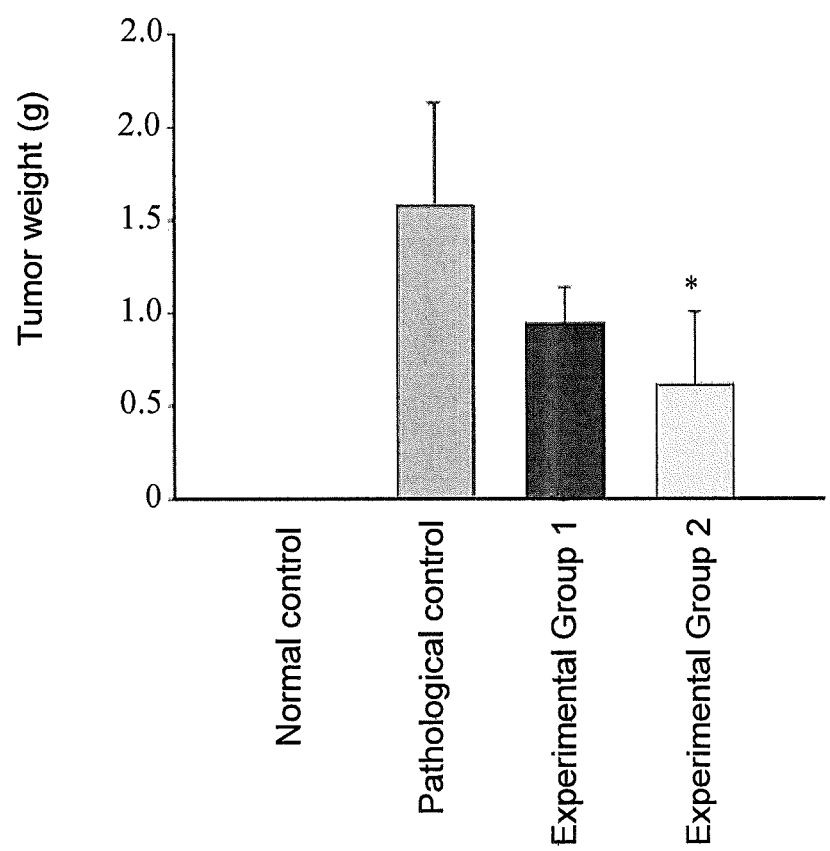
FIG. 8 shows the inhibitory effect of the refined product of the present disclosure upon the proliferation of mouse colon carcinoma cells, wherein the mice in the pathological control group were injected with mouse CT26 colon carcinoma cells, the mice in Experimental Groups 1 and 2 were injected with the refined product of the present disclosure (respectively at doses of 5 mg/kg and 15 mg/kg) and mouse CT26 colon carcinoma cells, the mice in the normal control group received no treatment and were not injected with mouse CT26 colon carcinoma cells, and "*" indicates $p<0.05$ when compared to the pathological control group.

Referring to FIG. 8, the tumor weight of each of Experimental Groups 1 and 2 is lower than that of the pathological control group. Particularly, there is a statistically significant difference between the tumor weight of Experimental Group 2 and that of the pathological control group. The aforesaid results reveal that the refined product of the present disclosure is effective in inhibiting the proliferation of colon carcinoma cells in mice.

B. Effect of Refined Product of Present Disclosure Upon Metastasis of Mouse Colon Carcinoma Cells The male BALB/c mice were randomly divided into the following groups (n=8 for each group): a sham-operated group, a pathological control group, and two experimental groups referred to as Experimental Groups 1 and 2. Each mouse in the pathological control group and Experimental Groups 1 and 2 was anesthetized with ether, and the left upper abdomen of each mouse was disinfected using 75% ethanol. Subsequently, the skin was incised using a surgical knife to expose the peritoneum under the skin, and an incision of about 1 cm was made in the peritoneum using the surgical knife. $1\times10^6$ CT26 cells were injected into the spleen, and the wound was stitched up.

The mice in the sham-operated group were generally subjected to the surgical procedures for the mice in the pathological control group and Experimental Groups 1 and 2, except that the spleen of each mouse in the sham-operated group was not injected with CT26 cells.

On the next day (i.e. the $2^{nd}$ day) after the injection of CT26 cells, the refined product solution obtained from section A of Example 3 was immediately administered to the mice in Experimental Groups 1 and 2 via intravenous injection respectively at a dose of 50 mg/kg and a dose of 100 mg/kg, and normal saline was administered to the mice in the pathological control group and the sham-operated group via intravenous injection at a dose of 10 mL/kg. The mice in each group were subjected to the once-a-day administration until the end of the $10^{th}$ day after the injection of CT26 cells.

On the $11^{th}$ day after the injection of CT26 cells, the mice in each group were anesthetized using $CO_2$ and were sacrificed. Then, the spleen and liver of each mouse were collected and weighted. The relative increase of spleen weight was determined by subtracting the spleen weight of the sham-operated group from that of the respective group. The relative increase of liver weight was determined by subtracting the liver weight of the sham-operated group from that of the respective group. Afterward, the data thus obtained were analyzed according to the method described in the "Statistical Analysis" section of "General Experimental Procedure". The results are shown in FIGS. 9 and 10.

Figure 9:
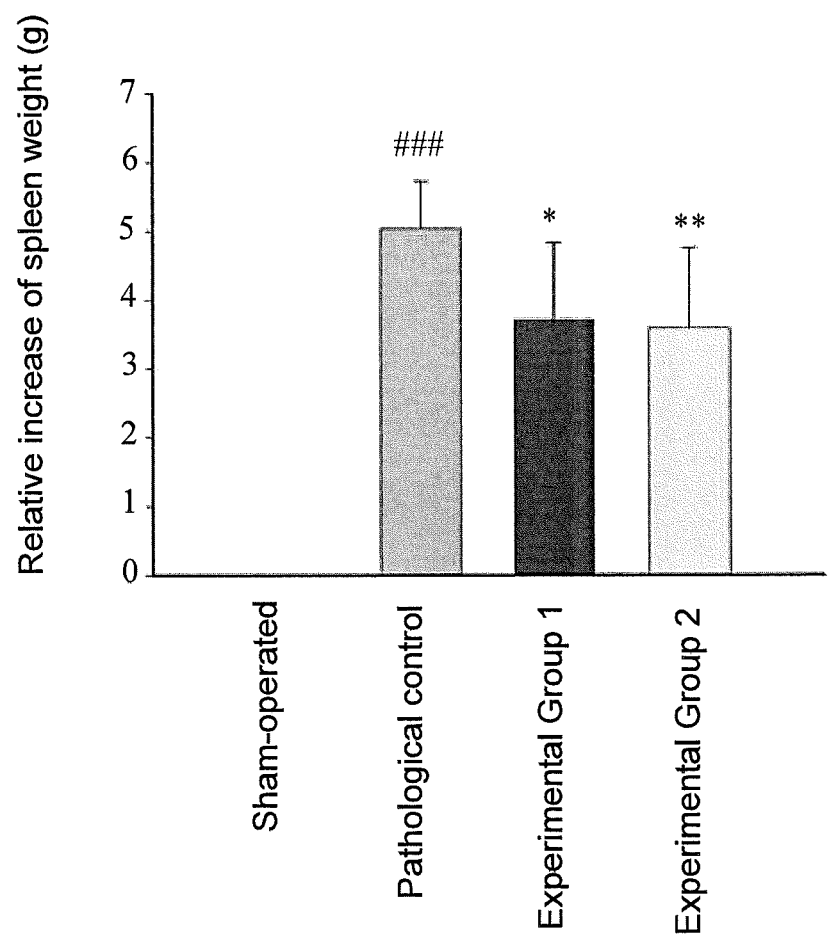
FIG. 9 shows the inhibitory effect of the refined product of the present disclosure upon the metastasis of mouse colon carcinoma cells, wherein the mice in the pathological control group were injected with mouse CT26 colon carcinoma cells, the mice in Experimental Groups 1 and 2 were injected with the refined product of the present disclosure (respectively at doses of 50 mg/kg and 100 mg/kg) and mouse CT26 colon carcinoma cells, the mice in the sham-operated group were not injected with mouse CT26 colon carcinoma cells, "###" indicates $p<0.001$ when compared to the sham-operated group, "*" indicates $p<0.05$ when compared to the pathological control group, and "**" indicates $p<0.01$ when compared to the pathological control group.
Figure 10:
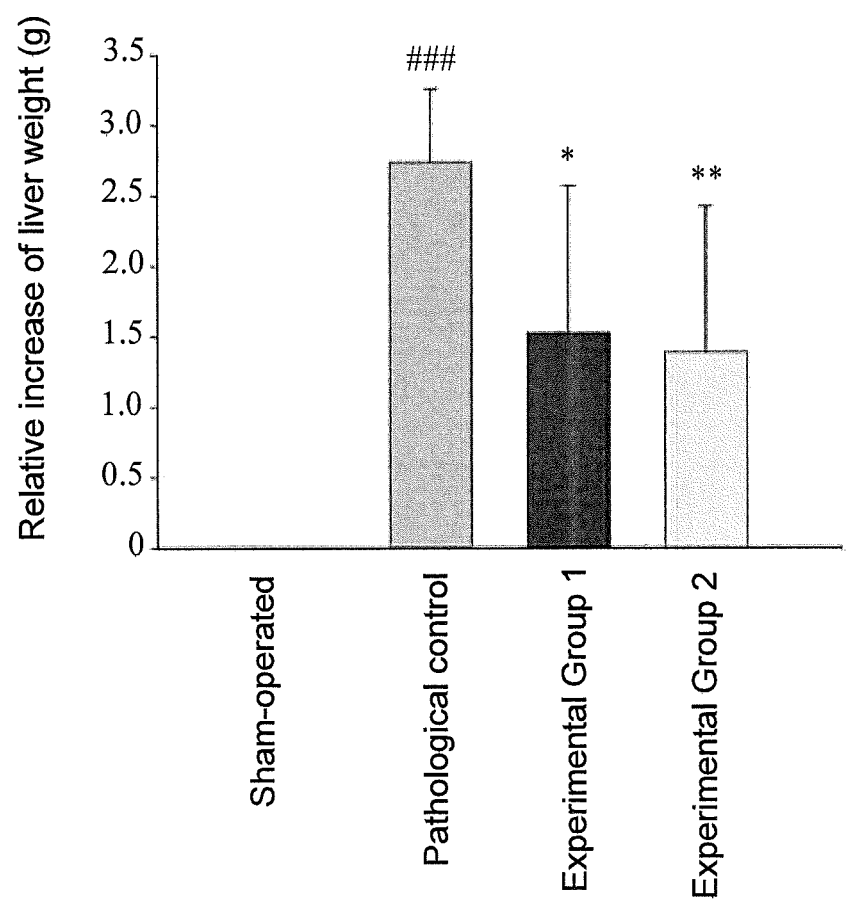
FIG. 10 shows the inhibitory effect of the refined product of the present disclosure upon the metastasis of mouse colon carcinoma cells, wherein the mice in the pathological control group were injected with mouse CT26 colon carcinoma cells, the mice in Experimental Groups 1 and 2 were injected with the refined product of the present disclosure (respectively at doses of 50 mg/kg and 100 mg/kg) and mouse CT26 colon carcinoma cells, the mice in the sham-operated group were not injected with mouse CT26 colon carcinoma cells, "###" indicates $p<0.001$ when compared to the sham-operated group, "*" indicates $p<0.05$ when compared to the pathological control group, and "**" indicates $p<0.01$ when compared to the pathological control group.

Referring to FIGS. 9 and 10, the relative increase of spleen weight and the relative increase of liver weight regarding each of Experimental Groups 1 and 2 are significantly lower than those regarding the pathological control group. The aforesaid results indicate that in mice, the refined product of the present disclosure can inhibit not only the proliferation of colon carcinoma cells in the spleen, but also the metastasis of colon carcinoma cells to the liver.

C. Effect of Refined Product of Present Disclosure Upon Aberrant Crypts and Aberrant Crypt Foci Induced by Azoxymethane The male BALB/c mice were randomly divided into the following groups (n=8 for each group): a pathological control group, a positive control group, and two experimental groups referred to as Experimental Groups 1 and 2. The mice in each group were intraperitonealy injected with azoxymethane at a dose of 10 mg/kg once a day for two weeks.

On the first day after the beginning of the injection with azoxymethane, the refined product solution obtained from section A of Example 3 was orally administered to the mice in Experimental Groups 1 and 2 respectively at a dose of 5 mg/kg and at a dose of 15 mg/kg, aspirin was orally administered to the mice in the positive control group at a dose of 10 mg/kg, and deionized water was orally administered to the mice in the pathological control group at a dose of 10 mL/kg. The mice in each group were subjected to the once-a-day administration until the end of the $6^{th}$ week after the beginning of the injection with azoxymethane.

At the end of the $6^{th}$ week after the beginning of the injection with azoxymethane, the mice in each group were anesthetized using $CO_2$ and were sacrificed. Then, colons were collected, followed by rinsing with ice-cold saline. After the intestinal contents were removed, the colons were longitudinally sectioned using a surgical knife. Fixation with a fixative solution (4% paraformaldehyde prepared in PBS) was conducted for 24 hours. The colon tissues were subjected to staining using methylene blue, followed by observation under an optical microscope at 40× magnification. The number of aberrant crypts and the number of aberrant crypt foci were counted. Afterward, the data thus obtained were analyzed according to the method described in the "Statistical Analysis" section of "General Experimental Procedure". The results are shown in FIGS. 11 and 12.

Figure 11:
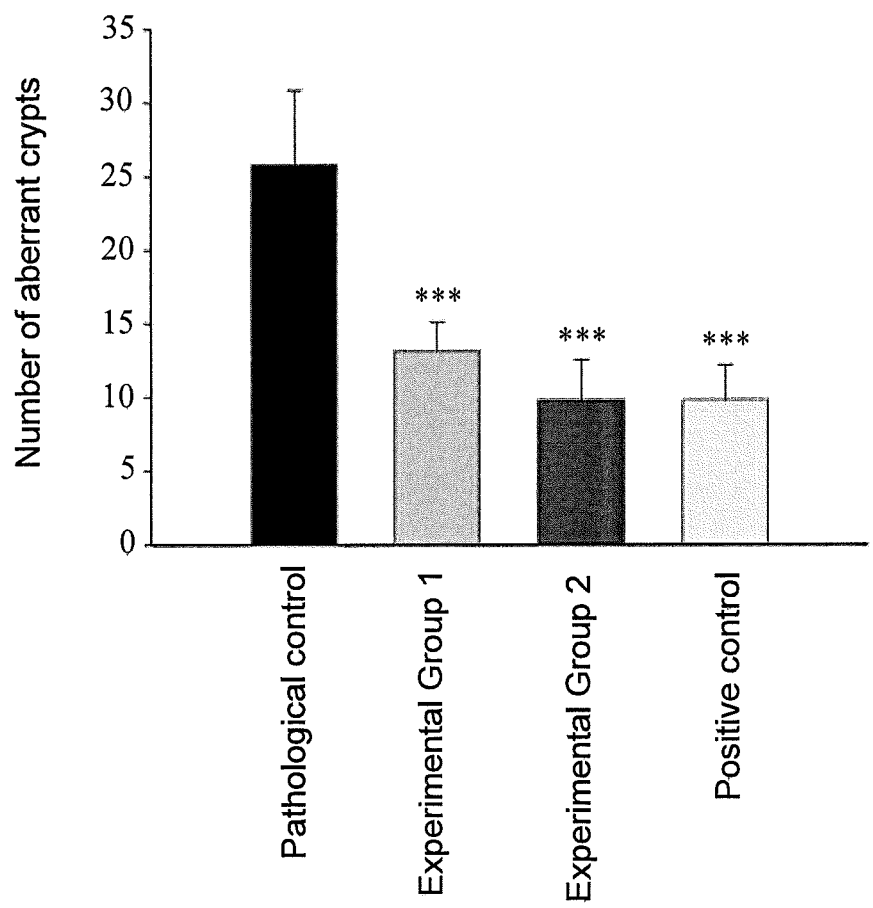
FIG. 11 shows the inhibitory effect of the refined product of the present disclosure on azoxymethane-induced aberrant crypts, wherein the mice in the pathological control group were induced to have aberrant crypts using azoxymethane, the mice in Experimental Groups 1 and 2 were induced to have aberrant crypts using azoxymethane and were subjected to oral administration of the refined product of the present disclosure (respectively at doses of 5 mg/kg and 15 mg/kg), the mice in the positive control group were induced to have aberrant crypts using azoxymethane and were subjected to oral administration of aspirin (at a dose of 10 mg/kg), and "*" indicates $p<0.001$ when compared to the pathological control group.
Figure 12:
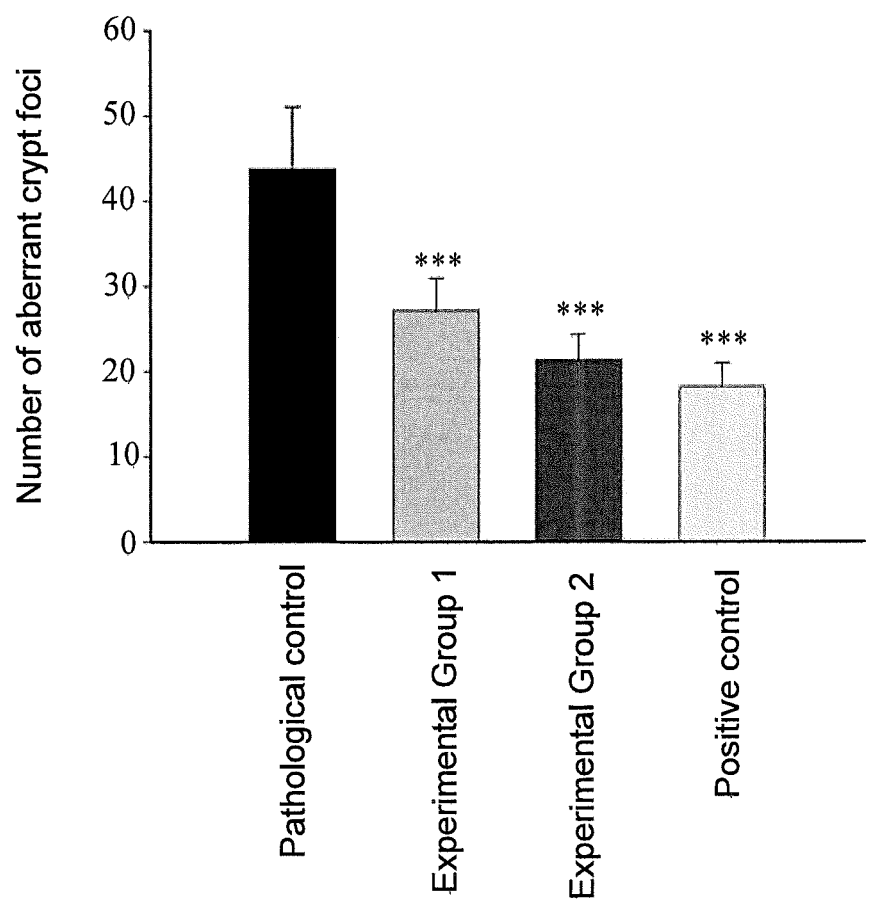
FIG. 12 shows the inhibitory effect of the refined product of the present disclosure on azoxymethane-induced aberrant crypt foci, wherein the mice in the pathological control group were induced to have aberrant crypt foci using azoxymethane, the mice in Experimental Groups 1 and 2 were induced to have aberrant crypt foci using azoxymethane and were subjected to oral administration of the refined product of the present disclosure (respectively at doses of 5 mg/kg and 15 mg/kg), the mice in the positive control group were induced to have aberrant crypt foci using azoxymethane and were subjected to oral administration of aspirin (at a dose of 10 mg/kg), and "*" indicates $p<0.001$ when compared to the pathological control group.

Referring to FIGS. 11 and 12, the number of aberrant crypts and the number of aberrant crypt foci regarding each of Experimental Groups 1 and 2 are significantly lower than those regarding the pathological control group. Particularly, the number of aberrant crypts and the number of aberrant crypt foci regarding Experimental Group 2 are close to those regarding the positive control group. The aforesaid results reveal that the refined product of the present disclosure is effective in improving the aberrant crypts and aberrant crypt foci induced by azoxymethane.

In view of the foregoing, the inventor deems that the refined product of the present disclosure can inhibit the in vivo proliferation and metastasis of colon carcinoma cells and prevent the formation of colon carcinoma cells.

Example 5

Evaluation for Synergistic Anticancer Effect of Refined Product of Present Disclosure and 5-fluorouracil (5-FU) on Colon Carcinoma Cells The male BALB/c mice were randomly divided into the following groups (n=8 for each group): a normal control group, a pathological control group, a 5-FU group, and a synergy group. $1\times10^6$ CT26 cells were subcutaneously injected into the leg of each mouse in the pathological control group, the 5-FU group, and the synergy group. The mice in the normal control group received no CT26 cells.

After the injection of CT26 cells, the mice in the 5-FU group, the synergy group, and the pathological control group were subjected to the treatments shown in Table 8 until the end of the $3^{rd}$ week after the injection of CT26 cells. The mice in the normal control group received no treatment.

TABLE 8

| | 5-FU group | Synergy group | Pathological control group |
| --- | --- | --- | --- |
| Treatment substance 1 | 5-FU | 5-FU | saline |
| Dosage | 10 mg/kg | 10 mg/kg | 10 mL/kg |
| Route | | Intraperitoneal injection | |
| Frequency | | Once every three days | |
| Treatment substance 2 | Deionized water | Refined Product solution[a] | Deionized water |
| Dosage | 30 mL/kg | 30 mg/kg | 30 mL/kg |
| Route | | Oral administration | |
| Frequency | | Once a day | |

[a]The refined product solution was obtained from section A of Example 3.

At the end of the $3^{rd}$ week after the injection of CT26 cells, the mice in each group were anesthetized using $CO_2$, and blood was collected from the celiac vein. The blood collected was subjected to total white blood cell counting using an automated hematology analyzer (Sysmex, KX-21 N). Besides, tumors were collected and weighted. The results thus acquired are shown in Table 9.

Referring to Table 9, both the tumor weight and the number of total white blood cells regarding the 5-FU group are significantly lower than those regarding the pathological control group, thereby indicating that although 5-FU exhibits an anti-cancer effect, the same leads to a side effect, i.e. reduction in the number of total white blood cells. Compared to the 5-FU group, the tumor weight regarding the synergy group is significantly lower, and the number of total white blood cells regarding the synergy group is significantly higher. The aforesaid results reveal that the refined product of the present disclosure not only can enhance the anti-cancer effect of 5-FU, but also can reduce the side effect of 5-FU.

TABLE 9

| Group | Number of total white blood cells[a] | Tumor weight[a] |
|---|---|---|
| Normal control group | 8.05 ± 0.39 | 0 ± 0 |
| Pathological control group | 6.59 ± 1.46 | 4.10 ± 0.92 |
| 5-FU group | 4.46 ± 0.77 | 3.19 ± 1.47 |
| Synergy group | 5.33 ± 0.60 | 2.34 ± 0.85 |

[a]The data are expressed as mean ± S.D.

Example 6

Evaluation for Therapeutic Effect of Refined Product of Present Disclosure on Ovalbumin-induced Allergy In order to examine whether the refined product of the present disclosure has an anti-allergy effect, the refined product prepared in Example 1 was used in the following experiments.

Experimental Procedures:

A. Treatment of Mice Having Ovalbumin-Induced Allergy with Refined Product of Present Disclosure The male BALB/c mice were randomly divided into the following groups (n=10 for each group): a normal control group, a pathological control group, and three experimental groups referred to as Experimental Groups 1 to 3. The refined product solution obtained from section A of Example 3 was orally administered to the mice in Experimental Groups 1 to 3 respectively at a dose of 5 mg/kg, a dose of 15 mg/kg, and a dose of 30 mg/kg, and deionized water was orally administered to the mice in the pathological control group at a dose of 10 mL/kg. The mice in Experimental Groups 1 to 3 and the pathological control group were subjected to the once-a-day administration for 8 weeks. The mice in the normal control group received no treatment.

At the end of the $6^{th}$ week after the beginning of the treatment, the mice in Experimental Groups 1 to 3 and the pathological control group were intraperitonealy injected with 100 μL of ovalbumin (in PBS; 50 μg/mouse) and 2 μL of Freund's complete adjuvant. At the end of the $8^{th}$ week after the beginning of the treatment, the mice in Experimental Groups 1 to 3 and the pathological control group were intraperitonealy injected with 6 μL of Freund's incomplete adjuvant so as to induce allergy. The mice in the normal control group were not subjected to induction of allergy.

At the $24^{th}$ hour after the injection with Freund's incomplete adjuvant, blood was collected from the facial vein by virtue of puncture. The blood collected was subjected to centrifugation at 4° C. and 4,700 rpm for 10 minutes. The serum thus obtained was used for the following enzyme linked immunosorbent assay (ELISA).

B. ELISA

100 μL of 10 μg/mL ovalbumin (in PBS) was added into a respective well of a 96-well plate, followed by standing at 4° C. overnight. The resultant supernatant was removed from the respective well, and the respective well was washed with a washing buffer (0.1% Tween 20 in PBS) thrice. 200 μL of 1% FBS (in PBS) was added into the respective well, followed by incubation at room temperature for 2 hours. The supernatant thus formed was removed from the respective well, and the respective well was washed with the abovementioned washing buffer thrice. 200 μL of the serum obtained from section A of this example, which was diluted 20 fold with PBS, was added into the respective well, and the reaction was allowed to proceed at room temperature for 2 hours. The resultant supernatant was removed from the respective well, and the respective well was washed with the abovementioned washing buffer thrice. 200 μL of biotinylated anti-mouse IgE antibody (eBioscience, Cat no. 13-5992) was added into the respective well, followed by mixing evenly. The reaction was allowed to proceed at room temperature for 2 hours. Thereafter, the supernatant thus formed was removed from the respective well, and the respective well was washed with 300 μL of the abovementioned washing buffer thrice. 100 μL of avidin-peroxidase conjugate (Millipore, Cat. No. 189728) was added into the respective well, followed by mixing evenly. The reaction was allowed to proceed at room temperature for 2 hours. 100 μL of TMB peroxidase substrate (eBioscience, Cat. No. 00-4201-56) was added into the respective well, followed by 30 minutes of incubation at room temperature for color development. The reaction was terminated using 50 μL of 2N $H_2SO_4$. Lastly, the absorbance at 450 nm ($OD_{450}$) was determined using an ELISA reader (TRIAD LT, Dynex). It should be noted that the higher the absorbance, the higher the IgE antibody content is. The data thus obtained were analyzed according to the method described in the "Statistical Analysis" section of "General Experimental Procedure".

Results:

$OD_{450}$ of each group is shown in Table 10. Referring to Table 10, $OD_{450}$ of the pathological control group is significantly higher than that of the normal control group, thereby indicating that ovalbumin successfully caused the mice to have allergy. Moreover, $OD_{450}$ of each of Experimental Groups 1 to 3 is significantly lower than that of the pathological control group. The aforesaid results reveal that the refined product of the present disclosure is effective in improving the ovalbumin-induced allergy in mice.

TABLE 10

| Group | $OD_{450}$[a] |
|---|---|
| Normal control group | 0.08 ± 0.01 |
| Pathological control group | 0.12 ± 0.01[##] |
| Experimental Group 1 | 0.11 ± 0.00** |
| Experimental Group 2 | 0.10 ± 0.00** |
| Experimental Group 3 | 0.10 ± 0.00** |

[a]The data are expressed as mean ± S.D.
[##]$p < 0.01$ when compared to the normal control group.
**$p < 0.01$ when compared to the pathological control group.

All patents and literature references cited in the present specification are hereby incorporated by reference in their entirety. In case of conflict, the present description, including definitions, will prevail.

While the present disclosure has been described with reference to the above specific embodiments, it is apparent that numerous modifications and variations can be made without departing from the scope and spirit of the present disclosure. It is therefore intended that the present disclosure be limited only as indicated by the appended claims.

We claim:

1. A process for producing a refined product from a rice hull, comprising:
   subjecting a rice hull to extraction with an aqueous solution so as to obtain an aqueous extract;
   admixing the aqueous extract with a first alcohol so as to obtain a first precipitate;
   subjecting the first precipitate to an enzymatic hydrolysis treatment so as to obtain an aqueous enzymatic hydrolysate, the enzymatic hydrolysis treatment employing an aqueous composition containing α-amylase, protease, and amyloglucosidase;
   admixing the aqueous enzymatic hydrolysate with a second alcohol so as to obtain a second precipitate; and
   refining the second precipitate by anion exchange chromatography, such that the refined product thus obtained consists essentially of a type II arabinogalactan having a number average molecular weight in the range of 56 to 103 kDa.

2. The process of claim 1, wherein the rice hull is obtained from a rice plant selected from *Oryza sativa, Oryza officinalis, Oryza nivara, Oryza rufipogon, Oryza punctata, Oryza glaberrima, Oryza australiensis, Oryza barthii, Oryza latifolia, Oryza longistaminata, Oryza meridionalis, Oryza brachyantha, Oryza eichingeri, Oryza grandiglumis*, and *Oryza minuta*.

3. The process of claim 1, wherein the first and second alcohols are identical, and are selected from the group consisting of methanol, ethanol, propanol, and combinations thereof.

4. The process of claim 1, wherein the first and second alcohols are different, and are selected from the group consisting of methanol, ethanol, propanol, and combinations thereof.

* * * * *